US012691264B2

(12) United States Patent
McDaniel et al.

(10) Patent No.: US 12,691,264 B2
(45) Date of Patent: Jul. 28, 2026

(54) MEDICAL DEVICES FOR SHUNTS, OCCLUDERS, FENESTRATIONS AND RELATED SYSTEMS AND METHODS

(71) Applicant: W. L. Gore & Associates, Inc., Newark, DE (US)

(72) Inventors: Tom R. McDaniel, Flagstaff, AZ (US); Edward E. Shaw, Flagstaff, AZ (US)

(73) Assignee: W. L. Gore & Associates, Inc., Newark, DE (US)

( * ) Notice: Subject to any disclaimer, the term of this patent is extended or adjusted under 35 U.S.C. 154(b) by 932 days.

(21) Appl. No.: 16/709,129

(22) Filed: Dec. 10, 2019

(65) Prior Publication Data

US 2020/0179663 A1    Jun. 11, 2020

Related U.S. Application Data

(60) Provisional application No. 62/777,931, filed on Dec. 11, 2018.

(51) Int. Cl.
*A61M 27/00* (2006.01)

(52) U.S. Cl.
CPC ... *A61M 27/002* (2013.01); *A61M 2202/0478* (2013.01); *A61M 2205/0238* (2013.01); *A61M 2205/0266* (2013.01); *A61M 2205/04* (2013.01); *A61M 2207/00* (2013.01); *A61M 2210/125* (2013.01)

(58) Field of Classification Search
CPC .. A61M 2202/0478; A61M 2205/0238; A61M 2205/0266; A61M 2205/04; A61M 2207/00; A61M 2210/125; A61M 27/002;

A61F 2/01; A61F 2230/001; A61F 2230/0058; A61F 2250/0039; A61F 2250/0051; A61B 17/0057; A61B 17/0218; A61B 2017/00252; A61B 2017/00592; A61B 2017/00597; A61B 2017/00606; A61B 2017/00623; A61B 2017/0225; A61B 2017/0237
See application file for complete search history.

(56) References Cited

U.S. PATENT DOCUMENTS

| | | |
|---|---|---|
| 5,276,276 A | 1/1994 | Gunn |
| 5,334,217 A | 8/1994 | Das |
| 5,683,411 A | 11/1997 | Kavteladze et al. |
| 5,824,055 A | 10/1998 | Spiridigliozzi et al. |

(Continued)

FOREIGN PATENT DOCUMENTS

| | | |
|---|---|---|
| CA | 2995185 A1 | 8/2018 |
| CN | 1819855 A | 8/2006 |

(Continued)

OTHER PUBLICATIONS

Eigler et al., "Cardiac Unloading with an Implantable Interatrial Shunt in Heart Failure: Serial Observations in an Ovine Model of Ischemic Cardiomyopathy", Structural Heart, vol. 1, No. (1-2), 2017, 'pp. 40-48.

(Continued)

*Primary Examiner* — Kai H Weng

(57) ABSTRACT

An implantable medical device comprising a first frame portion, a second frame portion arranged within the first frame portion and a plurality of diverging elements connecting the first frame portion to the second frame portion.

16 Claims, 20 Drawing Sheets

<u>1500</u>

(56)         References Cited

U.S. PATENT DOCUMENTS

| | | | |
|---|---|---|---|
| 5,944,738 | A | 8/1999 | Amplatz et al. |
| 6,042,602 | A | 3/2000 | Wells |
| 6,042,605 | A | 3/2000 | Martin et al. |
| 6,077,291 | A | 6/2000 | Das |
| 6,080,182 | A | 6/2000 | Shaw et al. |
| 6,461,665 | B1 | 10/2002 | Scholander |
| 6,616,675 | B1 | 9/2003 | Evard et al. |
| 6,911,037 | B2 | 6/2005 | Gainor et al. |
| 6,926,670 | B2 | 8/2005 | Rich et al. |
| 7,001,409 | B2 | 2/2006 | Amplatz |
| 7,049,380 | B1 | 5/2006 | Chang et al. |
| 7,128,073 | B1 | 10/2006 | Van et al. |
| 7,236,821 | B2 | 6/2007 | Cates et al. |
| 7,462,675 | B2 | 12/2008 | Chang et al. |
| 7,871,659 | B2 | 1/2011 | Cook et al. |
| 7,887,562 | B2 | 2/2011 | Young et al. |
| 7,901,702 | B2 | 3/2011 | Schwarz |
| 8,021,331 | B2 | 9/2011 | Herweck et al. |
| 8,043,360 | B2 | 10/2011 | Mcnamara et al. |
| 8,048,440 | B2 | 11/2011 | Chang et al. |
| 8,091,556 | B2 | 1/2012 | Keren et al. |
| 8,480,707 | B2 | 7/2013 | Pavcnik et al. |
| 8,545,525 | B2 | 10/2013 | Surti et al. |
| 8,696,693 | B2 | 4/2014 | Najafi et al. |
| 8,715,300 | B2 | 5/2014 | Najafi et al. |
| 8,728,103 | B2 | 5/2014 | Surti et al. |
| 9,241,695 | B2 | 1/2016 | Peavey et al. |
| 9,314,556 | B2 | 4/2016 | Tuseth |
| 9,358,371 | B2 | 6/2016 | Mcnamara et al. |
| 9,399,085 | B2 | 7/2016 | Cleek et al. |
| 9,456,812 | B2 | 10/2016 | Finch et al. |
| 9,545,300 | B2 | 1/2017 | Cully et al. |
| 9,554,786 | B2 | 1/2017 | Carley et al. |
| 9,629,715 | B2 | 4/2017 | Nitzan et al. |
| 9,636,094 | B2 | 5/2017 | Aurilia et al. |
| 9,649,481 | B2 | 5/2017 | Sadanand |
| 9,681,948 | B2 | 6/2017 | Levi et al. |
| 9,757,107 | B2 | 9/2017 | Mcnamara et al. |
| 9,775,591 | B2 | 10/2017 | Delgado et al. |
| 9,861,346 | B2 | 1/2018 | Callaghan |
| 9,878,162 | B2 | 1/2018 | Mika et al. |
| 9,949,728 | B2 | 4/2018 | Cahill |
| 10,806,458 | B2 | 10/2020 | Todd |
| 10,925,706 | B2 | 2/2021 | Eigler et al. |
| 2002/0077555 | A1 | 6/2002 | Schwartz |
| 2002/0077556 | A1 | 6/2002 | Schwartz |
| 2002/0169475 | A1 | 11/2002 | Gainor et al. |
| 2002/0173742 | A1 | 11/2002 | Keren et al. |
| 2003/0055344 | A1 | 3/2003 | Eigler et al. |
| 2003/0139819 | A1 | 7/2003 | Beer et al. |
| 2004/0049211 | A1 | 3/2004 | Tremulis et al. |
| 2004/0063805 | A1 | 4/2004 | Pacetti et al. |
| 2004/0073242 | A1 | 4/2004 | Chanduszko |
| 2005/0038351 | A1 | 2/2005 | Starobin et al. |
| 2005/0049675 | A1 | 3/2005 | Wallace |
| 2005/0148925 | A1 | 7/2005 | Rottenberg et al. |
| 2005/0283231 | A1 | 12/2005 | Haug et al. |
| 2006/0008500 | A1 | 1/2006 | Chavan et al. |
| 2006/0009800 | A1 | 1/2006 | Christianson et al. |
| 2006/0079736 | A1 | 4/2006 | Chin et al. |
| 2006/0100687 | A1 | 5/2006 | Fahey et al. |
| 2006/0116590 | A1 | 6/2006 | Fayram et al. |
| 2006/0198866 | A1 | 9/2006 | Chang et al. |
| 2006/0271116 | A1 | 11/2006 | Stahmann et al. |
| 2007/0032734 | A1 | 2/2007 | Najafi et al. |
| 2007/0118039 | A1 | 5/2007 | Bodecker et al. |
| 2007/0118213 | A1 | 5/2007 | Loulmet |
| 2007/0244518 | A1* | 10/2007 | Callaghan .......... A61B 17/0057 606/215 |
| 2007/0282430 | A1 | 12/2007 | Thommen et al. |
| 2008/0221551 | A1 | 9/2008 | Goodson et al. |
| 2008/0249562 | A1 | 10/2008 | Cahill |
| 2008/0262518 | A1 | 10/2008 | Freudenthal |
| 2008/0269551 | A1 | 10/2008 | Annest et al. |
| 2009/0024042 | A1 | 1/2009 | Nunez et al. |
| 2009/0030331 | A1 | 1/2009 | Hochareon et al. |
| 2009/0099640 | A1 | 4/2009 | Weng |
| 2009/0221923 | A1 | 9/2009 | Uemura et al. |
| 2009/0240427 | A1 | 9/2009 | Siereveld et al. |
| 2009/0319037 | A1 | 12/2009 | Rowe et al. |
| 2010/0049313 | A1 | 2/2010 | Alon et al. |
| 2010/0069778 | A1 | 3/2010 | Bornzin et al. |
| 2010/0094401 | A1 | 4/2010 | Kolbel et al. |
| 2011/0071623 | A1 | 3/2011 | Finch et al. |
| 2011/0071624 | A1 | 3/2011 | Finch et al. |
| 2011/0098767 | A1 | 4/2011 | Sugimachi et al. |
| 2011/0153010 | A1 | 6/2011 | Hanna |
| 2011/0184439 | A1 | 7/2011 | Anderson et al. |
| 2011/0257723 | A1 | 10/2011 | Mcnamara |
| 2011/0295183 | A1 | 12/2011 | Finch et al. |
| 2011/0295366 | A1 | 12/2011 | Finch et al. |
| 2011/0303229 | A1 | 12/2011 | Najafi et al. |
| 2012/0136385 | A1 | 5/2012 | Cully |
| 2012/0265296 | A1 | 10/2012 | Mcnamara et al. |
| 2013/0144379 | A1 | 6/2013 | Najafi et al. |
| 2013/0165967 | A1 | 6/2013 | Amin et al. |
| 2013/0178784 | A1 | 7/2013 | Mcnamara et al. |
| 2013/0281988 | A1 | 10/2013 | Magnin et al. |
| 2014/0012368 | A1 | 1/2014 | Sugimoto et al. |
| 2014/0018911 | A1 | 1/2014 | Zhou et al. |
| 2014/0107437 | A1 | 4/2014 | Pinsky |
| 2014/0128795 | A1 | 5/2014 | Keren et al. |
| 2014/0142617 | A1 | 5/2014 | Arsen et al. |
| 2014/0200662 | A1 | 7/2014 | Eftel et al. |
| 2014/0207153 | A1 | 7/2014 | Najafi et al. |
| 2014/0214149 | A1 | 7/2014 | Kuraguntla et al. |
| 2014/0222040 | A1 | 8/2014 | Park et al. |
| 2014/0228683 | A1 | 8/2014 | Aoki et al. |
| 2014/0343670 | A1 | 11/2014 | Bakis et al. |
| 2014/0371843 | A1 | 12/2014 | Wilson et al. |
| 2015/0039084 | A1 | 2/2015 | Levi et al. |
| 2015/0142049 | A1 | 5/2015 | Delgado et al. |
| 2015/0313596 | A1 | 11/2015 | Todd |
| 2015/0313599 | A1 | 11/2015 | Johnson et al. |
| 2016/0045165 | A1 | 2/2016 | Braido et al. |
| 2016/0058452 | A1 | 3/2016 | Brenneman et al. |
| 2016/0158000 | A1 | 6/2016 | Granada et al. |
| 2016/0263299 | A1 | 9/2016 | Xu et al. |
| 2016/0331566 | A1 | 11/2016 | Kheradvar et al. |
| 2017/0028194 | A1 | 2/2017 | Bonner et al. |
| 2017/0042705 | A1 | 2/2017 | Cook et al. |
| 2017/0105711 | A1 | 4/2017 | Masters |
| 2017/0106176 | A1 | 4/2017 | Taft et al. |
| 2017/0135817 | A1 | 5/2017 | Tylis et al. |
| 2017/0172766 | A1 | 6/2017 | Vong et al. |
| 2017/0196673 | A1 | 7/2017 | Cully et al. |
| 2017/0224323 | A1 | 8/2017 | Rowe et al. |
| 2017/0281339 | A1 | 10/2017 | Levi et al. |
| 2017/0319823 | A1 | 11/2017 | Yacoby et al. |
| 2017/0358942 | A1 | 12/2017 | Pugh et al. |
| 2018/0000580 | A1 | 1/2018 | Wallace et al. |
| 2018/0008830 | A1 | 1/2018 | Kaiser |
| 2018/0055629 | A1 | 3/2018 | Oba et al. |
| 2018/0098772 | A1 | 4/2018 | Goldshtein et al. |
| 2018/0126179 | A1 | 5/2018 | Haasl et al. |
| 2018/0160917 | A1 | 6/2018 | Liu et al. |
| 2018/0256865 | A1 | 9/2018 | Finch et al. |
| 2018/0280667 | A1 | 10/2018 | Keren |
| 2019/0130069 | A1 | 5/2019 | Li et al. |
| 2019/0231510 | A1 | 8/2019 | Rafiee et al. |
| 2019/0282178 | A1 | 9/2019 | Volosin et al. |
| 2019/0374343 | A1 | 12/2019 | Lashinski et al. |
| 2020/0038567 | A1 | 2/2020 | Siess et al. |
| 2020/0069426 | A1 | 3/2020 | Conklin et al. |
| 2020/0085378 | A1 | 3/2020 | Burnett et al. |
| 2020/0196876 | A1 | 6/2020 | Minor et al. |
| 2020/0196943 | A1 | 6/2020 | Minor et al. |
| 2020/0196944 | A1 | 6/2020 | Minor et al. |
| 2020/0197178 | A1 | 6/2020 | Vecchio |
| 2021/0259839 | A1 | 8/2021 | Cole et al. |
| 2021/0290214 | A1 | 9/2021 | Cole et al. |

(56) References Cited

U.S. PATENT DOCUMENTS

| | | | |
|---|---|---|---|
| 2024/0130624 A1 | 4/2024 | Kanjickal et al. |
| 2025/0186208 A1 | 6/2025 | Chang et al. |

FOREIGN PATENT DOCUMENTS

| | | |
|---|---|---|
| CN | 102271727 A | 12/2011 |
| CN | 104414692 A | 3/2015 |
| CN | 105473107 A | 4/2016 |
| CN | 107411848 A | 12/2017 |
| CN | 107847751 A | 3/2018 |
| CN | 108289737 A | 7/2018 |
| CN | 108451569 A | 8/2018 |
| CN | 108472142 A | 8/2018 |
| CN | 108697505 A | 10/2018 |
| CN | 110536657 A | 12/2019 |
| EP | 1264572 A1 | 12/2002 |
| EP | 2020248 A1 | 2/2009 |
| EP | 2637576 A1 | 9/2013 |
| GB | 1355373 A | 6/1974 |
| GB | 1506432 A | 4/1978 |
| GB | 1509023 A | 4/1978 |
| JP | 07-502918 A | 3/1995 |
| JP | 2000-505316 A | 5/2000 |
| JP | 2001-519694 A | 10/2001 |
| JP | 2002-248105 A | 9/2002 |
| JP | 2003-061917 A | 3/2003 |
| JP | 2003-519542 A | 6/2003 |
| JP | 2005-528181 A | 9/2005 |
| JP | 2006-528023 A | 12/2006 |
| JP | 2007-527742 A | 10/2007 |
| JP | 2008-512139 A | 4/2008 |
| JP | 2008-512211 A | 4/2008 |
| JP | 2008-545471 A | 12/2008 |
| JP | 2009-517137 A | 4/2009 |
| JP | 2010-505481 A | 2/2010 |
| JP | 2012-500665 A | 1/2012 |
| JP | 2013-517890 A | 5/2013 |
| JP | 2014-503246 A | 2/2014 |
| JP | 2014-151049 A | 8/2014 |
| JP | 2016-511656 A | 4/2016 |
| JP | 2016-518948 A | 6/2016 |
| JP | 2016-538094 A | 12/2016 |
| JP | 2017-513545 A | 6/2017 |
| JP | 2017-515631 A | 6/2017 |
| JP | 2017-536857 A | 12/2017 |
| JP | 2021-531097 A | 11/2021 |
| WO | 93/13712 A1 | 7/1993 |
| WO | 97/27898 A1 | 8/1997 |
| WO | 98/42276 A1 | 10/1998 |
| WO | 01/51123 A1 | 7/2001 |
| WO | 2003/103476 A2 | 12/2003 |
| WO | 2004/091411 A2 | 10/2004 |
| WO | 2005/074367 A2 | 8/2005 |
| WO | 2006/054343 A1 | 5/2006 |
| WO | 2007/062299 A2 | 5/2007 |
| WO | 2008/040555 A2 | 4/2008 |
| WO | 2009/137755 A2 | 11/2009 |
| WO | 2010/022138 A2 | 2/2010 |
| WO | 2011/093941 A2 | 8/2011 |
| WO | 2012/091809 A1 | 7/2012 |
| WO | 2014/018977 A1 | 1/2014 |
| WO | 2014/150106 A1 | 9/2014 |
| WO | 2015/109027 A2 | 7/2015 |
| WO | 2015/168501 A2 | 11/2015 |
| WO | 2017/118738 A1 | 7/2017 |
| WO | 2018/017900 A1 | 1/2018 |
| WO | 2020/018697 A1 | 1/2020 |

OTHER PUBLICATIONS

Feldman et al., "Transcatheter Interatrial Shunt Device for the Treatment of Heart Failure Rationale and Design of the Randomized Trial to Reduce Elevated Left Atrial Pressure in Heart Failure (Reduce LAP-HF I)", Circulation Heart failure, vol. 9, No. 7, 2016, pp. 1-10.

Gregg et al., "Interatrial Shunting for Heart Failure The V-Wave Shunt", Presentation at the Transcatheter Cardiovascular Therapeutics (TCT) Congress in Denver, Colorado, 2017, 18 pages.

Søndergaard et al., "Transcatheter treatment of heart failure with preserved or mildly reduced ejection fraction using a novel interatrial implant to lower left atrial pressure", European Journal of Heart Failure, vol. 16, 2014, pp. 796-801.

International Search Report and Written Opinion received for PCT Patent Application No. PCT/US2019/068277, mailed on Mar. 25, 2020, 13 pages.

International Search Report and Written Opinion received for PCT Patent Application No. PCT/US2019/068280, mailed on Mar. 25, 2020, 12 pages.

International Search Report and Written Opinion received for PCT Patent Application No. PCT/US2019/068282, mailed on Mar. 25, 2020, 15 pages.

International Preliminary Report on Patentability received for PCT Patent Application No. PCT/US2019/068275, mailed on Jul. 1, 2021, 11 pages.

International Preliminary Report on Patentability received for PCT Patent Application No. PCT/US2019/068277, mailed on Jul. 1, 2021, 7 pages.

International Preliminary Report on Patentability received for PCT Patent Application No. PCT/US2019/068280, mailed on Jul. 1, 2021, 7 pages.

International Preliminary Report on Patentability received for PCT Patent Application No. PCT/US2019/068282, mailed on Jul. 1, 2021, 9 pages.

International Search Report and Written Opinion received for PCT Patent Application No. PCT/US2019/068275, mailed on Jun. 25, 2020, 16 pages.

Kapur NK et al. Mechanical circulatory support devices for acute right ventricular failure. Circulation. 2017; 136:314-326 (Year: 2017).

International Search Report and Written Opinion received for PCT Patent Application No. PCT/US2019/042248, mailed on Oct. 23, 2019, 18 pages.

International Search Report and Written Opinion received for PCT Patent Application No. PCT/US2019/042252, mailed on Oct. 21, 2019, 18 pages.

International Search Report and Written Opinion received for PCT Patent Application No. PCT/US2021/013411, mailed on May 6, 2021, 11 pages.

Wei, X., Liu, X., Rosenzweig, A. What do we know about the cardiac benefits of exercise? Trends in Cardiovascular Medicine; 25(6) : 537-539. Aug. 2015 (Year: 2015).

Tanaka Hikaru, et al., "Shinzo No. Byouki to Chiryouaku", [online], Aug. 23, 2006, Internet URL: https://web.archive.org/web/20060823022639/https://www.mnc.tohou.ac.jp/v-lab/shinkin/medicine/medicine-1-2-1.html.

Tanaka et al., "A Pharmaceutical agent for the heart and drugs", Aug. 23, 2006, pp. 1-5.

* cited by examiner

300

400

600

1100

1300

1500

1500

1600

1600

1600

1700

1700

1800

1850

1880

1810

1810

MEDICAL DEVICES FOR SHUNTS, OCCLUDERS, FENESTRATIONS AND RELATED SYSTEMS AND METHODS

CROSS-REFERENCE TO RELATED APPLICATION

This application claims the benefit of Provisional Application No. 62/777,931, filed Dec. 11, 2018, which is incorporated herein by reference in its entirety for all purposes.

FIELD

The present disclosure relates generally to implantable medical devices, and more specifically to implantable medical devices for shunting and/or occluding bodily fluids or structures and related systems and methods thereof.

BACKGROUND

Heart failure and diseases of the heart affect millions of people worldwide. Heart failure includes failure of either the left side of the heart, the right side of the heart, or both. Diseases of the heart that can lead to heart failure include hypertension, pulmonary arterial hypertension, and congenital defects of the heart. The constantly evolving nature of heart failure represents a significant challenge for the treatment methods. Therefore, there is a need for new and adaptable methods and devices for treating heart failure.

SUMMARY

In one example ("Example 1"), an implantable medical device includes a first frame portion having at least three lobes; a second frame portion arranged within the first frame portion; and a plurality of diverging elements arranged between the first frame portion and the second frame portion, the plurality of diverging elements diverge from the first frame portion and the second frame portion to form a central frame with at least six diverging points in a deployed configuration.

In another example ("Example 2"), further to the device of Example 1, the first frame portion and the second frame are contiguous with one another.

In another example ("Example 3"), further to the device of any one of Examples 1-2, the opening is hexagonal in shape when the device is in a deployed configuration.

In another example ("Example 4"), further to the device of any one of Examples 1-3, the first frame portion is located on a first side of a septum, the second frame portion is located on a second side of the septum, and the plurality of diverging elements form a fluid flow path therethrough.

In another example ("Example 5"), further to the device of 4, the first and second frame portions are sufficiently flexible to conform to an anatomy of the septum.

In another example ("Example 6"), further to the device of any one of Examples 1-5, the second frame portion includes at least three lobes.

In another example ("Example 7"), further to the device of any one of Examples 1-6, the first frame portion has a first geometry and the second frame portion has a second geometry that is different from the first geometry.

In another example ("Example 8"), further to the device of any one of Examples 1-7, the first frame portion includes six lobes.

In another example ("Example 9"), further to the device of any one of Examples 1-8, each of the lobes of the second frame portion comprises an eyelet configured to aid in delivery of the device.

In another example ("Example 10"), further to the device of any one of Examples 1-9, the device also includes a covering material arranged on at least a portion of the device.

In another example ("Example 11"), further to the device of 10, the first frame portion includes the covering material and the second frame portion is free of the covering material.

In another example ("Example 12"), further to the device of 11, the covering material includes expanded polytetrafluoroethylene (ePTFE).

In another example ("Example 13"), further to the device of any one of Examples 1-12, the first frame portion and the second frame portion are unitary such that the device is formed of a single wire.

In another example ("Example 14"), further to the device of any one of Examples 1-13, the device also includes a sensor arranged with the conduit portion or the frame component and configured to sense at least one of physiologic properties, hemodynamics, biomarkers, sound, pressure, and electrolytes In another example ("Example 15"), further to the device of any one of Examples 1-14, the device also includes at least one of a coating of heparin to facilitate thromboresistance and patency of the device and a coating of paclitaxel to modulate tissue/cellular response.

In one example ("Example 16"), an implantable medical device for regulating blood pressure between a left atrium and a right atrium of a heart, the device having a delivery configuration and a deployed configuration includes a first frame portion; a second frame portion arranged within the first frame portion; and a plurality of diverging elements connecting the first frame portion to the second frame portion, the plurality of diverging elements form a central portion having an opening, and wherein the opening is substantially hexagonal in shape when the device is in the deployed configuration.

In another example ("Example 17"), further to the device of Example 16, each of the plurality of diverging elements overlaps one another to form diverging points, and wherein the diverging points expand outward when the device is in the deployed configuration to form the hexagonal shape.

In another example ("Example 18"), further to the device of Example 16, the first frame portion and the second frame portion are coplanar with one another when the device is in the deployed configuration, and are nonplanar with one another when the device is in the delivery configuration.

In one example ("Example 19"), a method of making the implantable medical device of any one of Examples 1 to 18 includes cutting a two-dimensional pattern out of a nitinol sheet.

In one example ("Example 20"), a method for regulating blood pressure between a left atrium and a right atrium of a heart includes delivering an implantable medical device to a desired treatment location within a body of a patient while the device is in a delivery configuration; positioning a first frame portion of the device on a first side of a septum; positioning a second frame portion of the device on a second side of the septum; and releasing the device from the delivery configuration to a deployed configuration such that a central portion of the device forms an opening that is substantially hexagonal in shape.

In another example ("Example 21"), further to the method of 20, the method also includes expanding the central portion to adjust a rate of fluid flow therethrough.

In one example ("Example 22"), an implantable medical device includes a first frame portion having at least two lobes; a second frame portion having at least two lobes; and a plurality of diverging elements arranged between the first frame portion and the second frame portion, the plurality of diverging elements diverge from the first frame portion and the second frame portion to form a central frame that is configured to approximate a circular shape in a deployed configuration.

In another example ("Example 23"), further to the medical device of Example 22, the central frame includes a polygonal structure configured to approximate the circular shape in the deployed configuration.

In another example ("Example 24"), further to the medical device of Example 22, the two lobes of the first frame portion are configured to conform to a first tissue surface and the two lobes of the second frame portion are configured to conform to a second tissue surface.

In another example ("Example 25"), further to the medical device of Example 22, the first and second frame portions are sufficiently flexible to conform to an anatomy of the septum.

The foregoing Examples are just that, and should not be read to limit or otherwise narrow the scope of any of the inventive concepts otherwise provided by the instant disclosure. While multiple examples are disclosed, still other embodiments will become apparent to those skilled in the art from the following detailed description, which shows and describes illustrative examples. Accordingly, the drawings and detailed description are to be regarded as illustrative in nature rather than restrictive in nature.

BRIEF DESCRIPTION OF THE DRAWINGS

The accompanying drawings are included to provide a further understanding of the disclosure and are incorporated in and constitute a part of this specification, illustrate embodiments, and together with the description serve to explain the principles of the disclosure.

DETAILED DESCRIPTION

Definitions and Terminology

Figure 1:
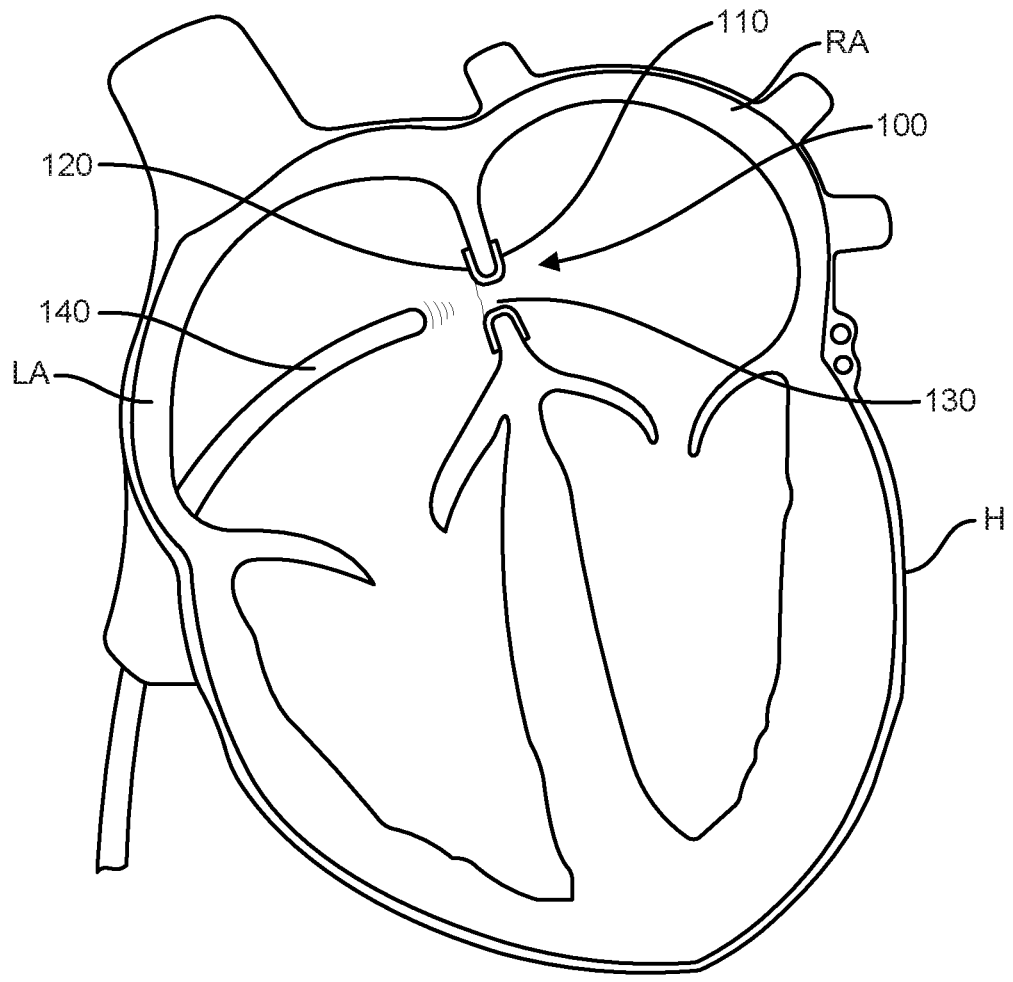
FIG. 1 is an example implantable medical device for regulating blood pressure, in accordance with an embodiment.

This disclosure is not meant to be read in a restrictive manner. For example, the terminology used in the application should be read broadly in the context of the meaning those in the field would attribute such terminology.

With respect to terminology of inexactitude, the terms "about" and "approximately" may be used, interchangeably, to refer to a measurement that includes the stated measurement and that also includes any measurements that are reasonably close to the stated measurement. Measurements that are reasonably close to the stated measurement deviate from the stated measurement by a reasonably small amount as understood and readily ascertained by individuals having ordinary skill in the relevant arts. Such deviations may be attributable to measurement error, differences in measurement and/or manufacturing equipment calibration, human error in reading and/or setting measurements, minor adjustments made to optimize performance and/or structural parameters in view of differences in measurements associated with other components, particular implementation scenarios, imprecise adjustment and/or manipulation of objects by a person or machine, and/or the like, for example. In the event it is determined that individuals having ordinary skill in the relevant arts would not readily ascertain values for such reasonably small differences, the terms "about" and "approximately" can be understood to mean plus or minus 10% of the stated value.

Description of Various Embodiments

Persons skilled in the art will readily appreciate that various aspects of the present disclosure can be realized by any number of methods and apparatuses configured to perform the intended functions. It should also be noted that the accompanying drawing figures referred to herein are not necessarily drawn to scale, but may be exaggerated to illustrate various aspects of the present disclosure, and in that regard, the drawing figures should not be construed as limiting.

Various aspects of the present disclosure are directed toward implantable medical devices such as devices for shunting and/or occluding bodily fluids or structures. In certain instances, the various aspects of the present disclosure relate to methods and devices for treating heart failure by reducing elevated blood pressure in a heart chamber by creating a pressure relief shunt. Additionally, some embodiments relate to methods and devices for customizing, adjusting or manipulating the flow of blood through the shunt in order to enhance the therapeutic effect of the pressure relief shunt. In some instances, the devices disclosed herein retain patency within the patient's body by reducing shear forces around the heart.

FIG. 1 is an example implantable medical device for regulating blood pressure implanted in a patient's body, in accordance with an embodiment. The device 100 is shown implanted within a heart H of the patient. The device 100 is shown arranged between the patient's left atrium LA and right atrium RA. In certain instances, the device 100 may be used to regulate blood flow within the heart H, for example, between the left and right atriums LA, RA. As shown, the device 100 generally includes a first frame portion 110 arranged on a first side of a septum (e.g., within the left atrium LA), a second frame portion 120 arranged on a second side of the septum (e.g., within the right atrium RA), and a central portion 130 extending through the septum. A needle may be used to create an opening in the septum.

A sheath 140 and constraining and/or release lines (not shown) may be used to facilitate deployment of the device 100. For example, a first side of the device 100 that includes the first frame portion 110 may be released after the sheath 190 is advanced through the septum and to the LA, and a second side of the device 100 that includes the second frame portion 120 may be released second on the RA side of the septum. The central portion 130 (e.g., shown in FIG. 2) is arranged within the opening. The first and second frame portions 110, 120 and the central portion 130 may be compressed within the sheath 190 to a delivery configuration such that the first and second frame portions 110, 120 are nonplanar with one another during delivery of the device 100 to the desired treatment area within the patient. The first and second frame portions 110, 120 may be subsequently expanded to a deployed configuration during deployment of the device 100 such that the first and second frame portions 110, 120 are coplanar with one another.

Figure 2:
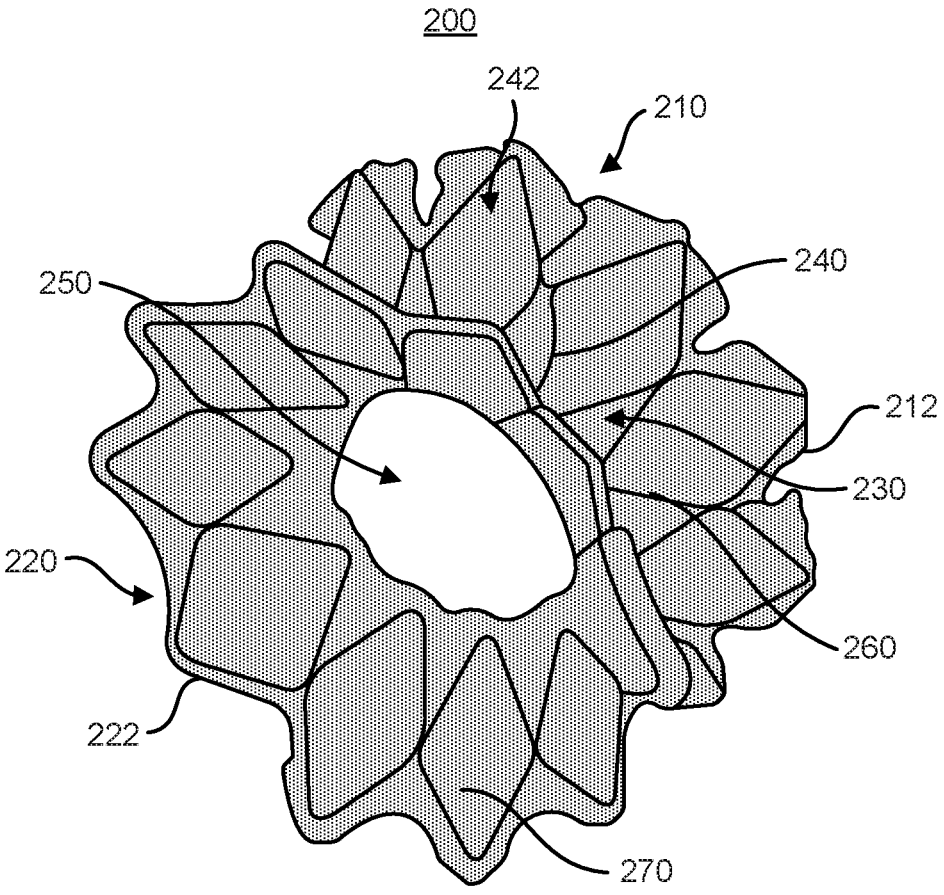
FIG. 2 is a perspective view of an implantable medical device, in accordance with an embodiment.

FIG. 2 is a perspective view of an implantable medical device 200 in the deployed configuration, in accordance with an embodiment. As described herein, the device includes the first frame portion 210 and the second frame portion 220. The first and second frame portions 210, 220 are sufficiently flexible to conform to the anatomy of the patient at the desired treatment location. For example, the first frame portion 210 can conform to the first side of the patient's septum (e.g., within the left atrium) and the second frame portion 220 can conform to the second side of the patient's septum (e.g., within the right atrium) as shown in FIG. 1. In some instances, the first frame portion 210 and second frame portion 220 include a first plurality of lobes 212 and a second plurality of lobes 222, respectively. In some instances, the first and second frame portions 210, 220 may include the same number of lobes or a different number of lobes as desired. For example, the first and second frame portions 210, 220 can both include two lobes, three lobes or four or more lobes as desired. As shown in FIG. 6 and FIGS. 9A-C, for example, the frame portions each include two lobes. In another example, the first frame portion 210 includes two lobes while the second frame portion 220 includes three or more lobes, and so on. The first and second frame portions 210, 220 can have any number of lobes as desired. In general, the number of lobes of the first and second frame portions 210, 220 can depend on the anatomy of the patient and the desired treatment location within the patient's body, among other factors.

The first and second frame portions 210, 220 can have a variety of geometries (e.g., shapes, sizes, lobe configurations, etc.). For example, in some instances, the first plurality of lobes 212 of the first frame portion 210 may have a first geometry while the second plurality of lobes 222 of the second frame portion 220 may have a second geometry that is different from the first geometry. For example, the first plurality of lobes 212 can be rhomboid in shape while the second plurality of lobes 222 can be rounded or petal-like. In another example, the first plurality of lobes 212 may be larger than the second plurality of lobes 222 and vice versa. In other instances, the first and second frame portions 210, 220 may have the same or substantially similar geometries. For example, the first and second frame portions 210, 220 can be substantially symmetrical.

As shown in FIG. 2, diverging elements 240 are arranged between the first and second frame portions 210, 220. In certain instances, the diverging elements 240 and the first and second frame portions 210, 220 are contiguous portions of a frame. In some instances, the diverging elements 240 are unitary with the first frame portion 210 and second frame portion 220. The diverging elements 240 are generally elongate members configured to span the septum of the patient and form the central portion 230 of the device 200 and a fluid flow path therethrough in a deployed configuration. For example, the first and second frame portions 210, 220 and the diverging elements 240 may be formed of a single wire. In other terms, the first and second frame portions 210, 220 are contiguous with one another.

In some instances, the diverging elements 240 cross over one another at certain locations in the central portion 230 to form diverging points 242. For example, in certain instances, the diverging elements 240 form at least six diverging points 242, which help to define an opening 250 through the device 200 or tissue. As detailed below, the device 200 may include a covering material 270. In instances where the device 200 does not have the covering material 270, the frame 200 may create and hold opening an opening 250 in tissue. In instances where the frame 200 includes the covering material 270, the opening 250 may be considered to be a portion of the device 200 with the covering material 270 forming the opening 250 or fluid pathway. The diverging points 242 also provide support and rigidity to the central portion 230 when the device 200 is in the deployed configuration. The diverging points 242 generally define an opening 250 that is hexagonal in shape, for example, when there are six diverging points 242 (e.g., each diverging point 242 forming a corner of the hexagon). However, the shape of the opening 250 (e.g., opening in tissue or device 200) will depend on the number of diverging points 242 within the central portion 230. For example, a device 200 having four diverging points 242 may have an opening 250 that is substantially rectangular in shape, or a device 200 having eight diverging points 242 may have an opening 250 that is octagonal in shape.

In some instances, the device 200 can be formed of a single wire. For example, the first and second frame portions 210, 220 and diverging elements 240 can be formed by wrapping a single wire (e.g., a Nitinol or stainless steel wire) in a desired shape or pattern. In some instances, the device 200 can be formed of a single sheet of flexible and biocompatible material. For example, a two-dimensional pattern may be cut from a flat sheet of Nitinol, stainless steel, or non-metallic material. In some instances, where a non-metallic material is used, the device 200 could be resorbable or biodegradable.

In some instances, the device 200 also includes a covering material 270. The covering material 270 may be, for example, a membrane material capable of promoting tissue ingrowth. In some instances, the membrane may also be configured to lessen erosion of the first frame portion 210 and/or the second frame portion 220. For example, the covering material 270 may be polytetrafluoroethylene (ePTFE) or any other suitable biocompatible material (e.g., polymeric or synthetic materials or woven materials).

In some instances, the covering material 270 covers at least a portion of the first frame portion 210 and/or at least a portion of the second frame portion 220. In some instances, both the first and second frame portions 210, 220 are completely covered by the covering material 270. In these instances, the covering material 270 may span the central portion 230. In some instances, the first frame portion 210 may include a first membrane material and the second frame portion 220 may include a second membrane material that is different from the first membrane material. In these instances, the first and second membrane materials may be coupled together at the central portion 230.

In some instances, the covering material 270 can be perforated to facilitate filtration and/or fluid flow through the device 200 to, for example, reduce the risk of stroke in certain patients. However, in other instances, where less fluid flow is desired, the covering material 270 may reduce or prevent fluid flow therethrough.

In certain instances, portions of the covering material 270 may be configured to inhibit tissue ingrowth (e.g., within the opening 250 through the device 200). In addition, portions of the covering material 270 arranged on the first plurality of lobes 212 and/or the second plurality of lobes 222 may be configured to facilitate tissue ingrowth to enhancing anchoring of the device 200 within the tissue. In addition, the first plurality of lobes 212 and/or the second plurality of lobes 222 may conform to a first tissue surface and a second tissue surface, respectively, such that tissue erosion is lessened and the first plurality of lobes 212 and/or the second plurality of lobes 222 react and move along with forces change the topography of the tissue.

In certain instances and as shown, the opening 250 through the device 200 includes a circumference that approximates a circle in shape. The diverging elements 240 cross over one another at certain locations in the central portion 230 such that a boundary or outer circumference of the opening 250 is approximately circular in shape. The diverging elements 240 may form a polygonal, structure, perimeter or boundary that approximates a circle. For example, the diverging elements 240 may include 8, 10, 12, 14, 16, 18, 20, 22, 24 or additional sides that form a polygonal structure, perimeter or boundary that approximates a circle in a deployed configuration. The opening 250 approximating having a perimeter or boundary that approximates a circle in shape may facilitating collapsing of the device to a delivery configuration while maintain hoop strength and lessen collapsing of the opening 250 in the deployed configuration. In the deployed configuration, the first frame portion 210 may be deployed on one side of a tissue structure and the second frame portion 220 may be deployed on another side of a tissue structure (e.g., as shown in FIGS. 9B-C.

Figure 3:
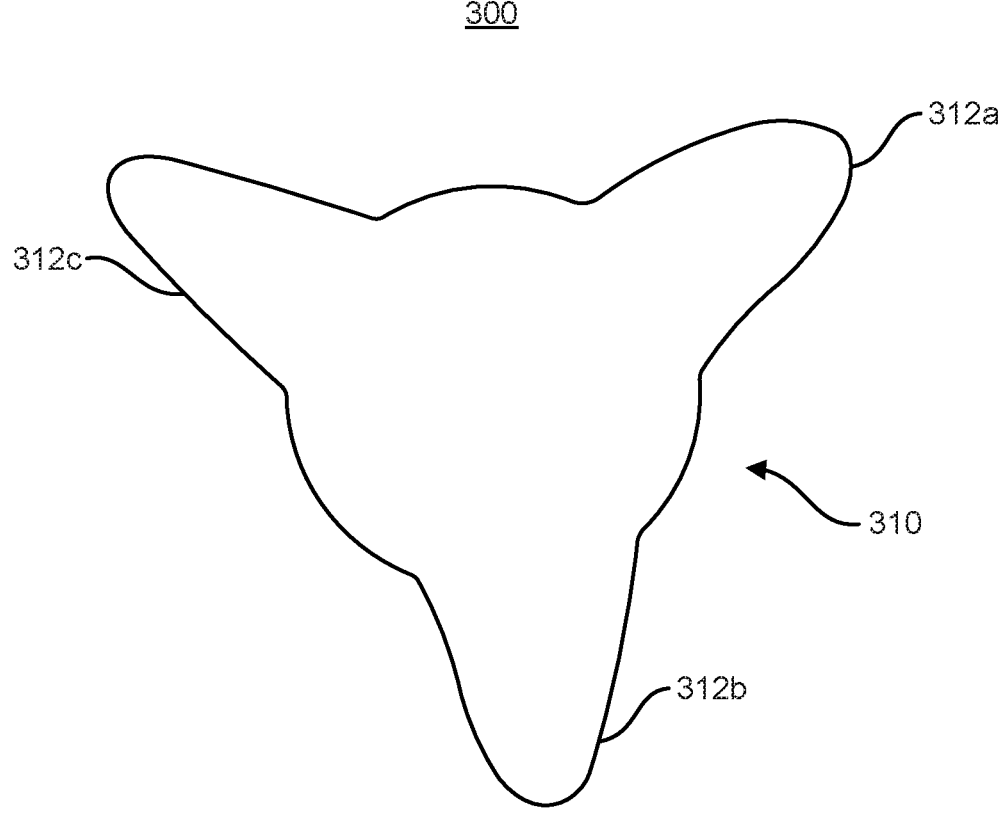
FIG. 3 is a top view of a first side of an implantable medical device, in accordance with an embodiment.

FIG. 3 is a top view of a first side of an implantable medical device 300, in accordance with an embodiment. As shown, the first frame portion 310 includes three lobes (e.g., a first lobe 312a, a second lobe 312b, and a third lobe 312c). The lobes may be spaced an equal distance apart from one another as shown such that each of the lobes are separate from one another. For example, each of the first, second, and third lobes 312a, 312b, 312c can move independently of one another to conform to the anatomy of the patient when the device 300 is in the deployed configuration.

Though not shown in FIG. 3, the second frame portion 320 can have the same or a different number of lobes as the first frame portion 310. For example, in some instances, the first and second frame portions 310, 320 each have three lobes. In other instances, the first frame portion 310 may include three lobes while the second frame portion 320 includes two, four, five or more lobes. In some instances, the first frame portion 310 can have lobes that are larger, smaller, and/or a different shape than the lobes of the second frame portion 320.

Figure 4:
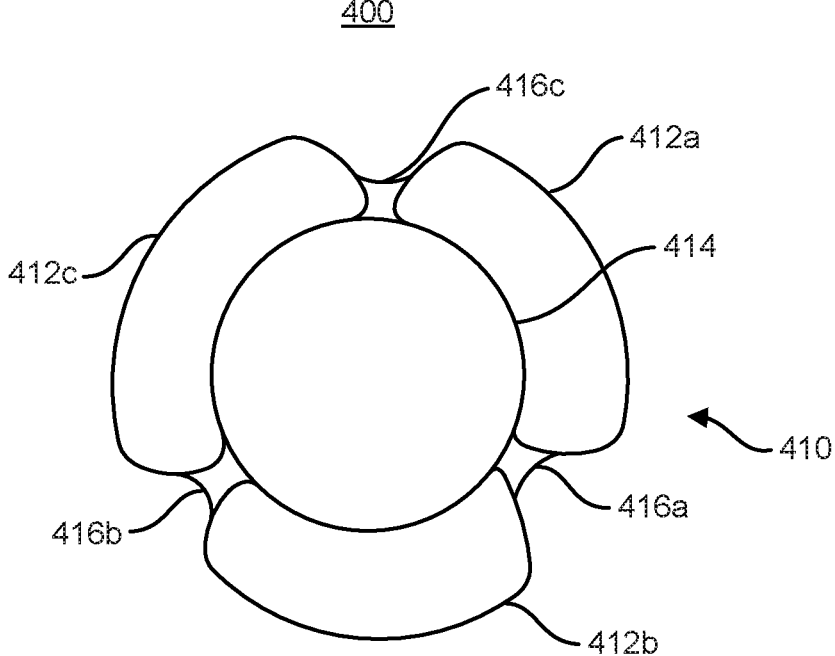
FIG. 4 is a top view of another implantable medical device, in accordance with an embodiment.

FIG. 4 is a top view of a first side of another implantable medical device 400, in accordance with an embodiment. As shown, the first frame portion 410 includes three lobes (e.g., a first lobe 412a, a second lobe 412b, and a third lobe 412c) and an inner frame portion 414. Each of the lobes 412a, 412b, and 412c may be attached to the inner frame portion 414 such that the lobes are equally spaced around the inner frame portion 414. In some instances, the lobes may be attached to the inner frame portion 414 and/or to adjacent lobes at attachment points 416a, 416b, and 416c. For example, in some instances, the first lobe 412a is attached to the second lobe 412b at attachment point 416a, the second lobe 412b is attached to the third lobe 412c at attachment point 416b, and the third lobe 412c is attached to the first lobe 412a at attachment point 416c. Although FIG. 4 is described with reference to three lobes and three attachment points, the first frame portion 410 can have any number of lobes and respective attachment points as desired. The first frame portion 410 and the second frame portion 420 are formed by diverging elements of a continuous or contiguous frame. The first frame portion 410 and the second frame portion 420 may be formed of a cut-tube, wound wire, or other similar structure.

Though not shown in FIG. 4, the second frame portion 420 can have the same or a different number of lobes as the first frame portion 410. For example, in some instances, the first and second frame portions 410, 420 each have three lobes. In other instances, the first frame portion 410 may include two, three lobes while the second frame portion 420 includes two, four, five or more lobes. In some instances, the first frame portion 410 can have lobes that are larger, smaller, and/or a different shape than the lobes of the second frame portion 420.

In certain instances, portions of the device 400 may include covering material as described in detail above with reference to FIG. 2. As discussed with reference to FIG. 2, the covering material may be configured to inhibit tissue ingrowth (e.g., within the inner frame portion 414 through the device 400). In addition, the first frame portion 410 and/or the second frame portion 420 may conform to a first tissue surface and a second tissue surface, respectively, such that tissue erosion is lessened and the first frame portion 410 and/or the second frame portion 420 react and move along with forces change the topography of the tissue.

In certain instances and as shown, the inner frame portion 414 through the device 400 includes a circumference that approximates a circle in shape. The inner frame portion 414 may form a polygonal structure, perimeter or boundary that approximates a circle. For example, the inner frame portion 414 may include 8, 10, 12, 14, 16, 18, 20, 22, 24 or additional sides that form a polygonal perimeter or boundary that approximates a circle in a deployed configuration. The inner frame portion 414 approximating having a perimeter or boundary that approximates a circle in shape may facilitating collapsing of the device to a delivery configuration while maintain hoop strength and lessen collapsing of the inner frame portion 414 in the deployed configuration. In the deployed configuration, one or more of the lobes 412a, 412b, 412c may be deployed on one side of a tissue structure and other ones of the lobes 412a, 412b, 412c may be deployed on another side of a tissue structure (e.g., as shown in FIGS. 9B-C. The inner frame portion 414 may provide a lumen through with fluid may flow and may also hold open the tissue.

Figure 5:
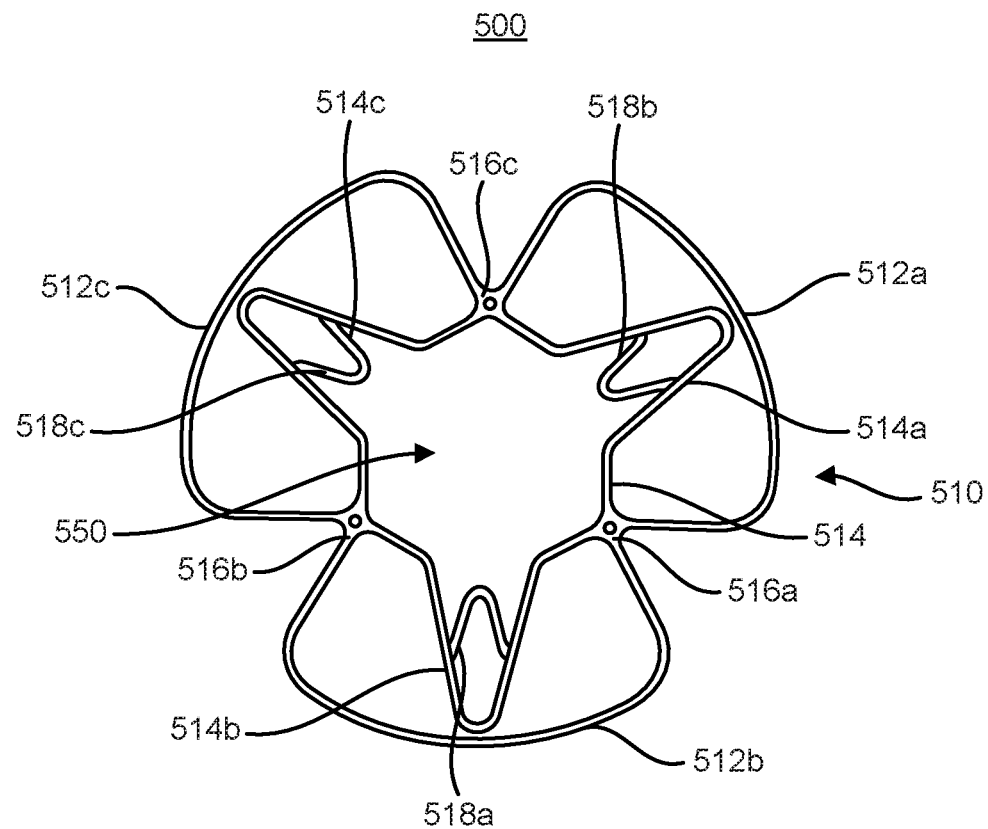
FIG. 5 is a top view of another implantable medical device, in accordance with an embodiment.

FIG. 5 is a top view of a first side of another implantable medical device 500, in accordance with an embodiment. As shown, the first frame portion 510 includes three lobes (e.g., a first lobe 512a, a second lobe 512b, and a third lobe 512c) and an inner frame portion 514. Each of the lobes 512a, 512b, and 512c may be attached to the inner frame portion 514 such that the lobes are equally spaced around the inner frame portion 514. In some instances, the lobes may be attached to the inner frame portion 514 and/or to adjacent lobes at attachment points 516a, 516b, and 516c. For example, in some instances, the first lobe 512a is attached to the second lobe 512b at attachment point 516a, the second lobe 512b is attached to the third lobe 512c at attachment point 516b, and the third lobe 512c is attached to the first lobe 512a at attachment point 516c. Although FIG. 5 is described with reference to three lobes and three attachment points, the first frame portion 510 of the device 500 can have any number of lobes and respective attachment points as desired.

The inner frame portion 514 can be any shape as desired. For example, in some instances, the inner frame portion 514 is substantially circular (e.g., as shown in FIG. 4) or substantially triangular (FIG. 5). In some instances, the inner frame portion 514 can define inner lobes 514a, 514b, and 514c, which may extend into the first, second and third lobes 512a, 512b, 512c to define the shape of the inner frame portion 514.

Though not shown in FIG. 5, the second frame portion 520 can have the same or a different number of lobes as the first frame portion 510. For example, in some instances, the first and second frame portions 510, 520 each have three lobes. In other instances, the first frame portion 510 may include three lobes while the second frame portion 520 includes two, four, five or more lobes. In some instances, the first frame portion 510 can have lobes that are larger, smaller, and/or a different shape than the lobes of the second frame portion 520.

In certain instances, the device 500 may include stiffeners 518a, 518b, 518c. The stiffeners 518a, 518b, 518c are arranged inside inner lobes 514a, 514b, and 514c (and may be included in any of the lobes of devices discussed herein. The stiffeners 518a, 518b, 518c form diamond cells in the inner lobes 514a, 514b, and 514c that collapse and open during load and deployment of the device 500 in a catheter. The stiffeners 518a, 518b, 518c may enhance radial strength during deployment and facilitate arrangement of the device 500 in a deployed and intended shape.

In certain instances and as shown, an opening 550 through the device 500 includes a circumference that approximates a circle in shape. A boundary or outer circumference of the opening 550 is approximately circular in shape. The first frame portion 510 and/or the second frame portion 520, when deployed, may form a polygonal structure, perimeter or boundary for the opening 550 that approximates a circle. For example, the opening 550 may include 8, 10, 12, 14, 16, 18, 20, 22, 24 or additional sides that form a polygonal structure, perimeter or boundary that approximates a circle in a deployed configuration. The opening 550 approximating having a perimeter or boundary that approximates a circle in shape may facilitating collapsing of the device to a delivery configuration while maintain hoop strength and lessen collapsing of the opening 550 in the deployed configuration. In the deployed configuration, the first frame portion 510 may be deployed on one side of a tissue structure and the second frame portion 520 may be deployed on another side of a tissue structure (e.g., as shown in FIGS. 9B-C. The first frame portion 510 and the second frame portion 520 are formed by diverging elements of a continuous or contiguous frame. The first frame portion 510 and the second frame portion 520 may be formed of a cut-tube, wound wire, or other similar structure.

Figure 6:
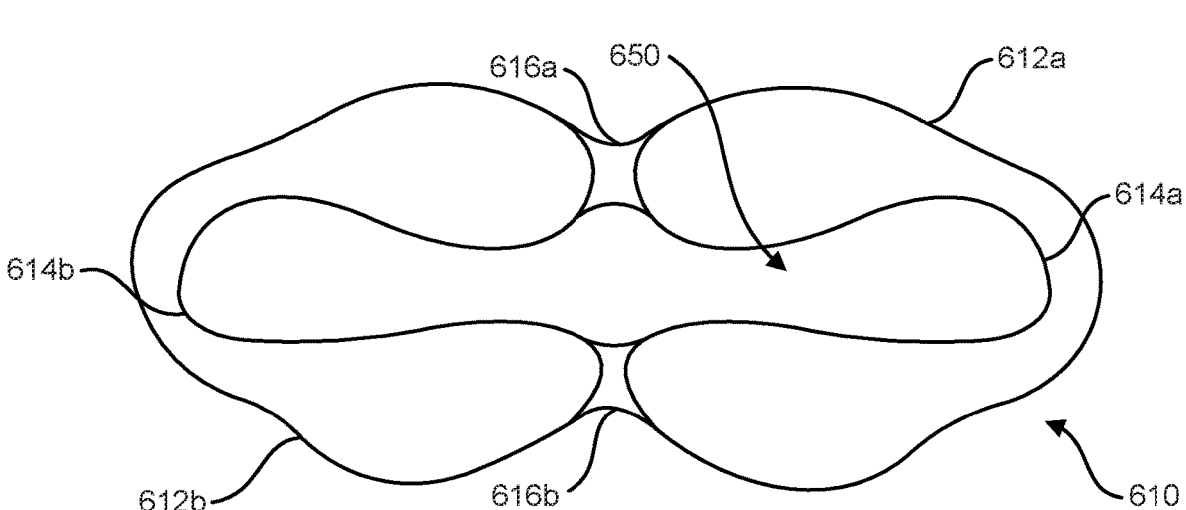
FIG. 6 is a top view of a first side of another implantable medical device, in accordance with an embodiment.

FIG. 6 is a top view of a first side of another implantable medical device 600, in accordance with an embodiment. As shown, the first frame portion 610 includes two lobes (e.g., a first lobe 612a and a second lobe 612b). A first inner frame portion 614a of the first lobe 612a and a second inner frame portion 614b of the second lobe 614b define the opening 650. The opening 650 may be any shape as desired. However, the shape of the opening 650 generally depends upon the shape of the first and second lobes 612a, 612b. For example, in some instances, the opening 650 may be substantially ovular, rectangular or oblong in shape, while in other instances, the opening 650 can be more circular in shape. The first frame portion 610 and the second frame portion 620 may be formed by diverging elements of a continuous or contiguous frame. The first frame portion 610 and the second frame portion 620 may be formed of a cut-tube, wound wire, or other similar structure.

The first and second lobes 612a, 612b may be integral with one another. For example, the first and second lobes 612a, 612b may be unitary such that the lobes are formed out of a single wire. In some instances, the first lobe 612*a* and the second lobe 612*b* may be formed separately from one another. For example, the first lobe 612*a* may be formed of a first wire and the second lobe 612*b* may be formed of a second wire, and the lobes may be attached at first and second attachment points 616*a*, 616*b*, as shown in FIG. 6.

Though not shown in FIG. 6, the second frame portion 620 can have the same or a different number of lobes as the first frame portion 610. For example, in some instances, the first and second frame portions 610, 620 each have three lobes. In other instances, the first frame portion 610 may include three lobes while the second frame portion 620 includes two, four, five or more lobes. In some instances, the first frame portion 610 can have lobes that are larger, smaller, and/or a different shape than the lobes of the second frame portion 620.

In certain instances, portions of the first frame portion 610 and/or the second frame portion 620 may include a covering material. The covering material may be configured to inhibit tissue ingrowth (e.g., within the opening 650 through the device 600). In addition, portions of the covering material arranged on the first frame portion 610 and/or the second frame portion 620 may be configured to facilitate tissue ingrowth to enhancing anchoring of the device 600 within the tissue. In addition, the lobes of the first frame portion 610 and the second frame portion 620 may conform to a first tissue surface and a second tissue surface, respectively, such that tissue erosion is lessened and the lobes react and move along with forces change the topography of the tissue. In the deployed configuration, the first frame portion 610 may be deployed on one side of a tissue structure and the second frame portion 620 may be deployed on another side of a tissue structure (e.g., as shown in FIGS. 9B-C.

Figure 7:
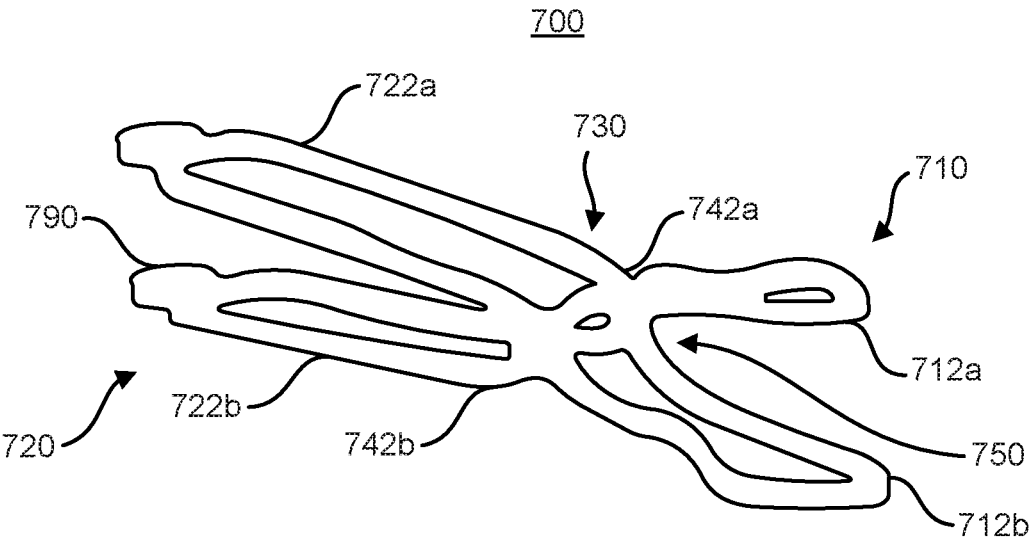
FIG. 7 is a perspective view of another implantable medical device, in accordance with an embodiment.

FIG. 7 is a perspective view of another implantable medical device 700, in accordance with an embodiment. The device 700 is shown in the delivery configuration with the first frame portion 710 and the second frame portion 720 folded in upon themselves to facilitate compaction of the device 700 for delivery to the desired treatment location. As shown, each side of the device 700 includes two lobes. For example, the first frame portion 710 includes a first lobe 712*a* and a second lobe 712*b*, and the second frame portion 720 includes a first lobe 722*a* and a second lobe 722*b*. The first and second frame portions 710, 720 are connected to one another at diverging points 742*a* and 742*b* to form a central portion 730 defining the opening 750.

One or more frame portions of the device 700 can include eyelets 790 to help facilitate delivery of the device. For example, each of the lobes of the first and/or second frame portions 710, 720 can include one or more eyelets 790. During delivery of the device 700, delivery lines could be threaded through the eyelets 790, for example, and tensioned to fold and/or compress the first and second frame portions 710, 720 into the delivery configuration. The eyelets 790 enable loading into a delivery catheter by interacting with tethers, wires, or other similar structures. The device 700 may be drawn into the catheter by the eyelets 790 and collapsed, for example, into the shape shown. In certain instances, the device 700 may include a post, ball, or an encapsulated frame element in place of the eyelets 790.

Once the device 700 is positioned at the desired treatment location, the first and second frame portions 710, 720 can be deployed (e.g., tension applied to the device 700 may be released) to release the lobes toward the septum of the patient (e.g., the first and second lobes 712*a*, 712*b* of the first frame portion 710 will release against the first side of the septum and the first and second lobes 722*a*, 722*b* of the second frame portion 720 will release against the second side of the septum).

Figure 8A:
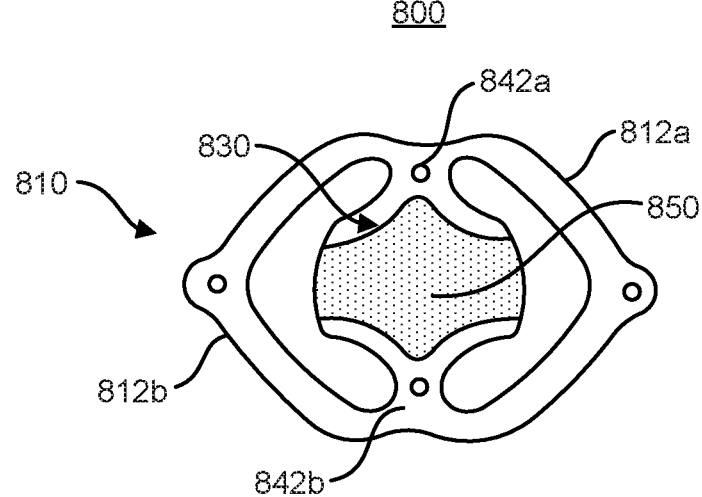
FIG. 8A is an image of a first side of an implantable medical device, in accordance with an embodiment.
Figure 8B:
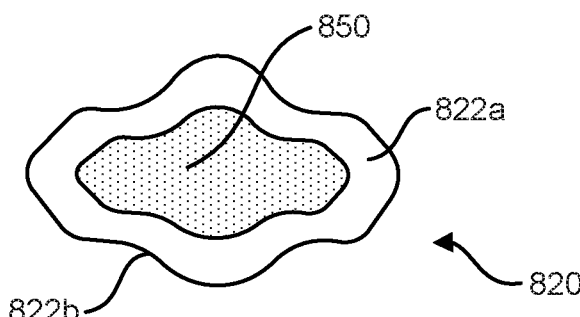
FIG. 8B is an image of a second side of the implantable medical device of FIG. 7A, in accordance with an embodiment.

FIG. 8A is an image of a first side of an implantable medical device 800 deployed at a desired treatment location, in accordance with an embodiment. FIG. 8B is an image of a second side of the implantable medical device 800 of FIG. 8A deployed at the desired treatment location, in accordance with an embodiment. As shown in FIG. 8A, the first frame portion 810 includes a first lobe 812*a* and a second lobe 812*b*. The second frame portion 820 (FIG. 8B) also includes a first lobe 822*a* and a second lobe 822*b*. In some instances, the first lobe 812*a* of the first frame portion 810 and the first lobe 822*a* of the second frame portion 820 are contiguous with one another. For example, the first lobes 812*a*, 822*a* are formed of a single, unitary wire that spans the septum and forms at least part of the central portion 830 of the device 800. The second lobe 812*b* of the first frame portion 810 and the second lobe 822*b* of the second frame portion 820 are also contiguous with one another. For example, the second lobes 812*a*, 822*a* are formed of a single, unitary wire that spans the septum and forms at least part of the central portion 830 of the device 800. As shown, the second frame portion 820 can have a different shape and size than the first frame portion 810. For example, in certain instances, the lobes 822*a*, 822*b* of the second frame portion 820 may have different shapes and/or sizes than the lobes 812*a*, 812*b* of the first frame portion 810.

Each of the first lobes 812*a*, 822*a* and the second lobes 812*b*, 822*b* are connected to one another at diverging points 842*a*, 842*b* to form a central portion 830 defining the opening 850. As shown, the opening 850 is generally ovular or oblong in shape. However, the opening 850 can be any shape as desired depending upon the shape and/or orientation of the first and second frame portions 810, 820 and the number of diverging points 842 in the central portion 830.

Figure 9A:
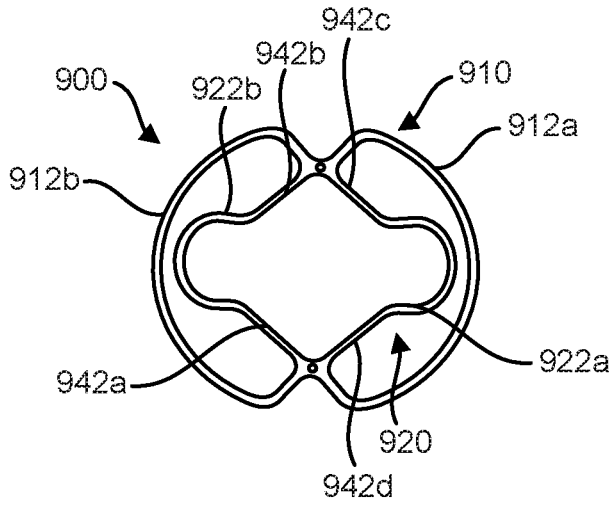
FIG. 9A is an image of an implantable medical device, in accordance with an embodiment.
Figure 9B:
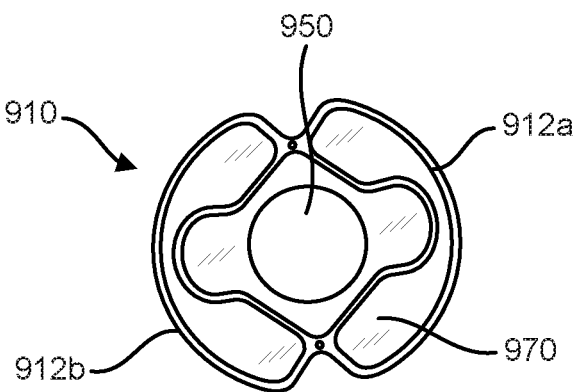
FIG. 9B is an image of a first side of the implantable medical device of FIG. 9A, with a membrane, in accordance with an embodiment.
Figure 9C:
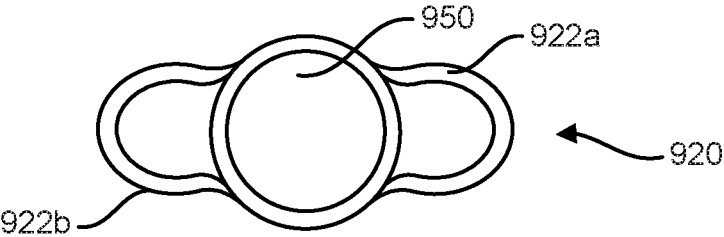
FIG. 9C is an image of a second side of the implantable medical device of FIGS. 9A-B, in accordance with an embodiment.

FIG. 9A is an image of an implantable medical device 900, in accordance with an embodiment. As shown, the device 900 is formed in a flat, 2-dimensional configuration. The first frame portion 910 includes two lobes (e.g., a first lobe 912*a* and a second lobe 912*b*). The second frame portion 920 is in the same plane as the first frame portion 910. As shown, the second frame portion 920 also includes two lobes (e.g., the first lobe 922*a* and second lobe 922*b*). In some instances, the first lobe 912*a* of the first frame portion 910 and the first lobe 922*a* of the second frame portion 920 are contiguous with one another. For example, the first lobes 912*a*, 922*a* are formed of a single, unitary wire. The second lobe 912*b* of the first frame portion 910 and the second lobe 922*b* of the second frame portion 920 are also contiguous with one another. For example, the second lobes 912*a*, 922*a* are formed of a single, unitary wire. As shown, the second frame portion 920 can have a different shape and/or size than the first frame portion 910. For example, the lobes 912*a*, 912*b* of the first frame portion may be larger and more elongate in shape than the lobes 922*a*, 922*b* of the second frame portion 920, which are smaller. Larger lobes 912*a*, 912*b* on one side (e.g., the left side) of the device 900 may prevent migration or dislodgement because pressure may be greater on the left side of the heart. The larger lobe 912*a*, 912*b* on the left side may absorb the higher pressure of the left side of the heart. The first frame portion 910 and the second frame portion 920 may be formed by diverging elements of a continuous or contiguous frame. The first frame portion 910 and the second frame portion 920 may be formed of a cut-tube, wound wire, or other similar structure.

FIG. 9B is an image of a first side of the implantable medical device 900 of FIG. 9A including a covering material 970, in accordance with an embodiment. In some instances, the first frame portion 910 includes the covering material 970 positioned over each of the lobes (e.g., the first lobe 912a and the second lobe 912b). The covering material 970 can be, for example, a membrane configured to promote tissue ingrowth to cover at least a portion of the first frame portion 910. The second frame portion 920 may or may not include the covering material 970.

FIG. 9C is an image of the second side of the implantable medical device 900 of FIG. 9A in the deployed configuration, in accordance with an embodiment. As shown in FIG. 9A, the first frame portion 910 includes the first lobe 912a and a second lobe 912b. The second frame portion 920 (FIG. 9B) also includes the first lobe 922a and a second lobe 922b. Each of the first lobes 912a, 922a and the second lobes 912b, 922b are connected to one another at diverging points 942a, 942b, 942c, 942d to form a central portion 930 defining the opening 950. As shown, the opening 950 is generally ovular or oblong in shape. However, the opening 950 can be any shape as desired depending upon the shape and/or orientation of the first and second frame portions 910, 920 and the number of diverging points 942 in the central portion 930.

In certain instances, portions of the covering material 970 may be configured to inhibit tissue ingrowth (e.g., within the opening 950 through the device 200). In addition, portions of the covering material 970 arranged on the first frame portion 910 and/or the second frame portion 920 may be configured to facilitate tissue ingrowth to enhancing anchoring of the device 900 within the tissue. In addition, each of the lobes of the first frame portion 910 and/or the second frame portion 920 may conform to a first tissue surface and a second tissue surface, respectively, such that tissue erosion is lessened and the lobes of the first frame portion 910 and/or the second frame portion 920 react and move along with forces change the topography of the tissue.

In certain instances and as shown, the opening 950 through the device 900 includes a circumference that approximates a circle in shape. A boundary or outer circumference of the opening 950 is approximately circular in shape. The first frame portion 910 and/or the second frame portion 920, when deployed, may form a polygonal structure, perimeter or boundary for the opening 950 that approximates a circle. For example, the opening 950 may include 8, 10, 12, 14, 16, 18, 20, 22, 24 or additional sides that form a polygonal structure, perimeter or boundary that approximates a circle in a deployed configuration. The opening 950 approximating having a perimeter or boundary that approximates a circle in shape may facilitating collapsing of the device to a delivery configuration while maintain hoop strength and lessen collapsing of the opening 950 in the deployed configuration.

Figure 10A:
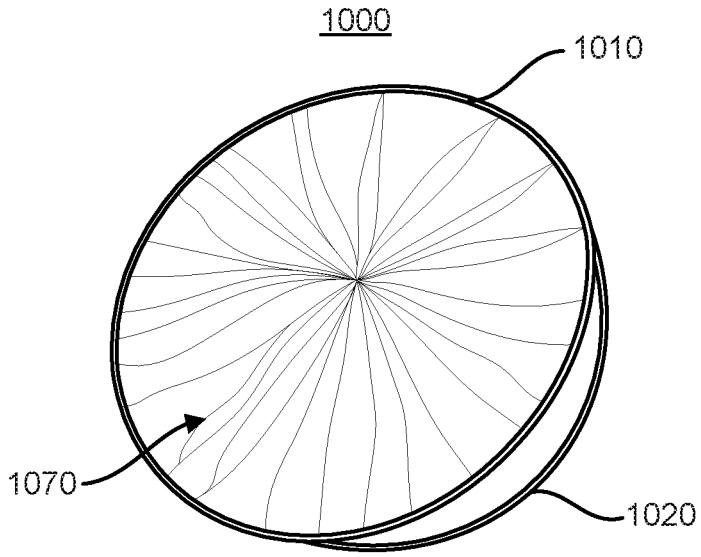
FIG. 10A is an image of an implantable medical device, in accordance with an embodiment.

FIG. 10A is an image of an implantable medical device 1000, in accordance with an embodiment. As shown, in some instances, both the first frame portion 1010 and second frame portion 1020 can include a covering material 1070. In certain instances, the covering material 1070 may be arranged on at least a portion of the first frame portion 1010 and/or the second frame portion 1020 and may span the central portion 1030. The first frame portion 1010 and second frame portion 1020, when covered with the covering material 1070, may form a first petal and a second petal respectively. As shown in FIG. 10A, the first frame portion 1010 and second frame portion 1020, when covered with the covering material 1070 to form petals, can be configured to flatten or longitudinally shorten. For example, the central portion 1030 (FIG. 10B) of the device can be configured to longitudinally shorten and compress such that the first and second frame portions 1010, 1020 are substantially flush with one another (e.g., with minimal separate between the first frame portion 1010 and second frame portion 1020).

Figure 10B:
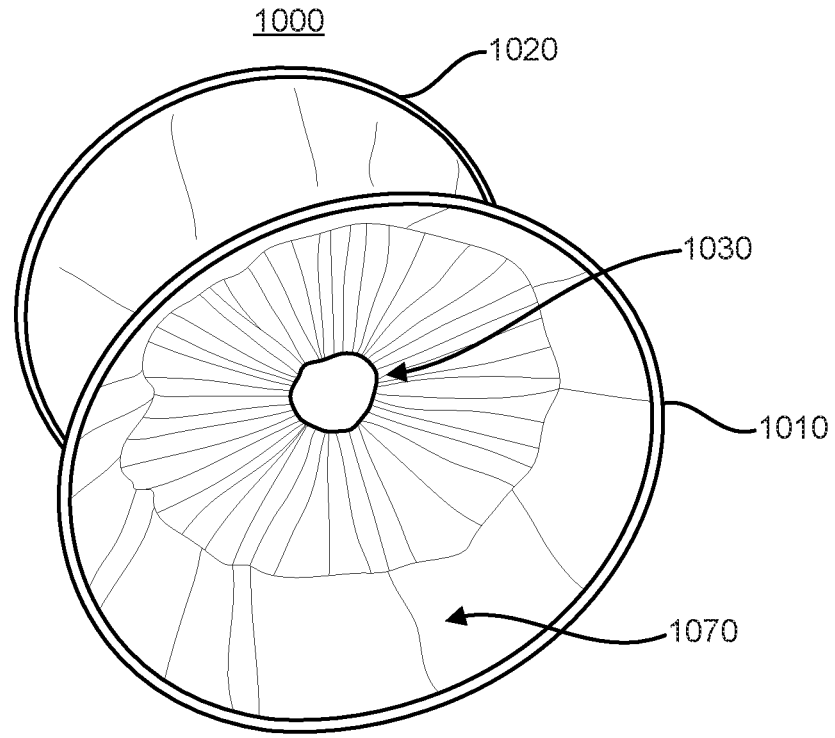
FIG. 10B is an image of the implantable medical device of FIG. 10A having an open central portion, in accordance with an embodiment.

As shown in FIG. 10B, the first frame portion 1010 and second frame portion 1020, when covered with the covering material 1070, may extend outwardly from the central portion 1030 to form cup like structures. In certain instances and as shown in FIG. 10B, the central portion 1030 can be configured to expand and lengthen longitudinally so that the device 1000 may span the septum of the patient.

Figure 11:
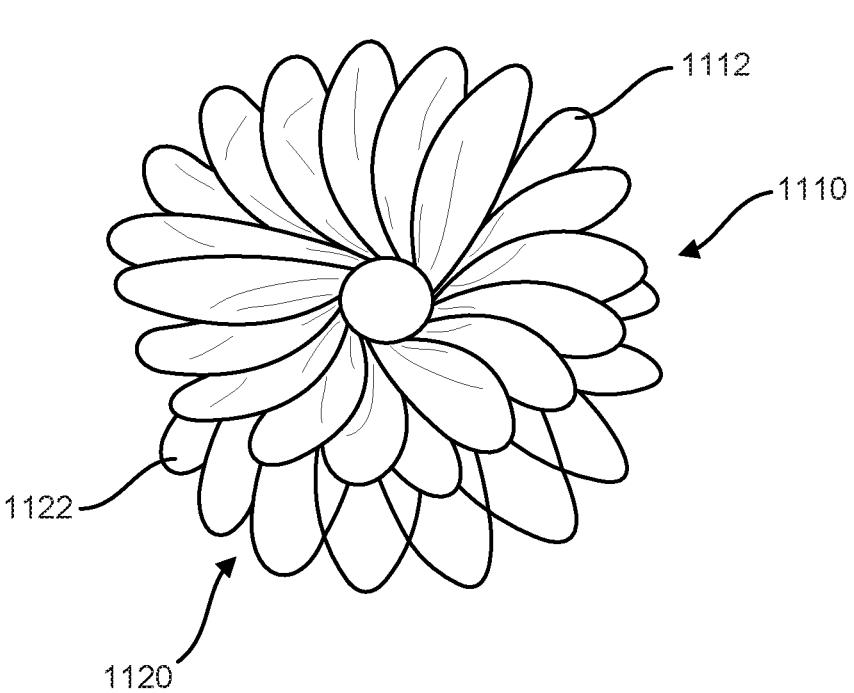
FIG. 11 is an image of another implantable medical device, in accordance with an embodiment.

FIG. 11 is an image of another implantable medical device 1100, in accordance with an embodiment. As shown, the first frame portion 1110 includes a first plurality of lobes 1112 arranged in an overlapping configuration. For example, each lobe of the first plurality of lobes 1112 at least partially overlaps an adjacent lobe. The second frame portion 1120 also includes a second plurality of lobes 1122 arranged in an overlapping configuration (e.g., each lobe of the second plurality of lobes 1122 at least partially overlaps an adjacent lobe).

Figure 12:
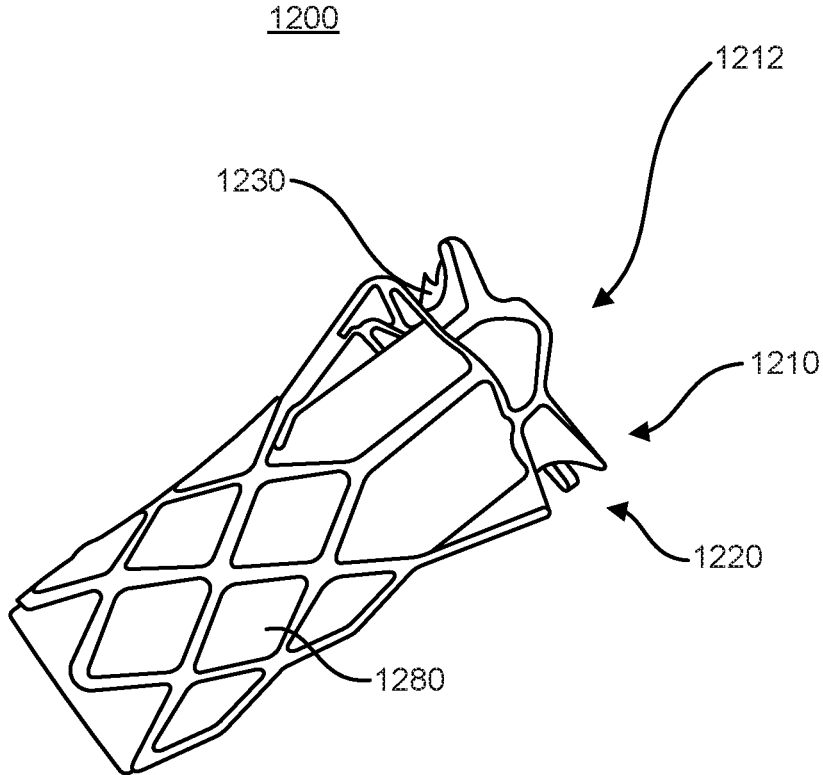
FIG. 12 is an image of another implantable medical device, in accordance with an embodiment.

FIG. 12 is an image of another implantable medical device 1200, in accordance with an embodiment. As shown, the device 1200 includes a first frame portion 1210 including a first plurality of lobes 1212. The first frame portion 1210 is connected to the second frame portion 1220 by diverging elements 1240 to form central portion 1230. The second frame portion 1220 includes a conduit portion 1280 extending from the second frame portion 1220 in the opposite direction of the first frame portion 1210. In some instances, the conduit portion 1280 can be positioned in a side branch of a vessel within the patient's body. In some instances, the conduit portion 1280 may form a lumen configured to facilitate fluid flow therethrough. In some instances, the conduit portion 1280 can also include a valve configured to control fluid flow through the lumen.

Figure 13:
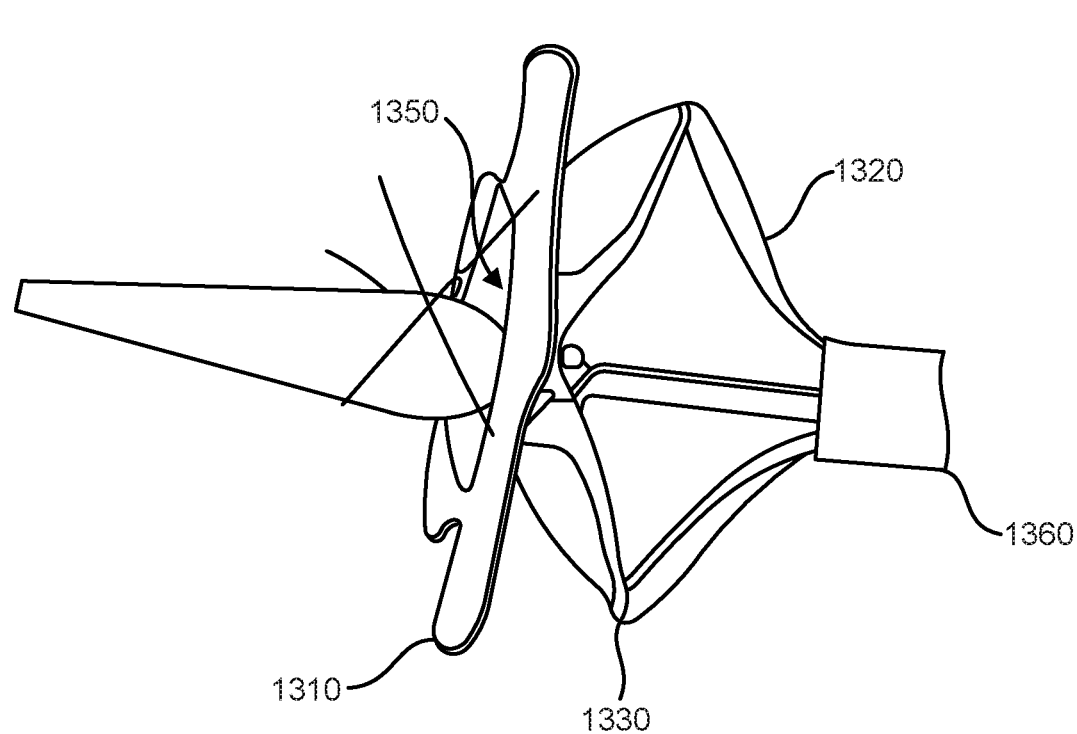
FIG. 13 is an image of an implantable medical device and a deployment apparatus, in accordance with an embodiment.

FIG. 13 is an image of a system for delivering the implantable medical device 1300 to the body of a patient, in accordance with an embodiment. As shown, the system may include a delivery device 1350 and a deployment mechanism 1360. In some instances, the deployment mechanism includes deployment lines configured to collapse the device 1300 into the delivery configuration.

In certain instances, the device 1300 can be loaded onto the delivery device 1350 such that the delivery device 1350 extends through the opening 1350 of the device 1300. The deployment lines can then be threaded through portions of the lobes of at least one of the first and second frame portions 1310, 1320. In some examples, the deployment lines may be threaded through eyelets formed in the lobes. The first and second frame portions are folded by advancement of the delivery device 1350 and collapsed into a low-profile delivery configuration.

The device 1300 can be delivered to the desired treatment location while in the delivery configuration. The first frame portion 1310 is then positioned on a first side of the septum and the second frame portion is positioned on a second side of the septum. Released of the second frame portion 1320 release is controlled by advancement and retraction of the delivery catheter.

In some instances, once deployed, the central portion 1330 of the device 1300 can be radially expanded or compressed to adjust the rate of fluid flow through the opening as desired.

Figure 14A:
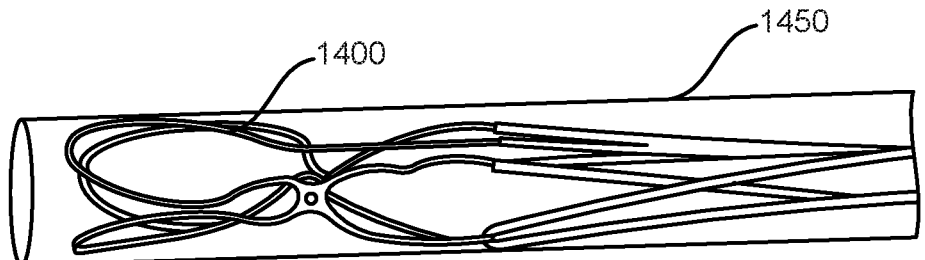
FIG. 14A is an image of an implantable medical device and a deployment apparatus, in accordance with an embodiment.
Figure 14B:
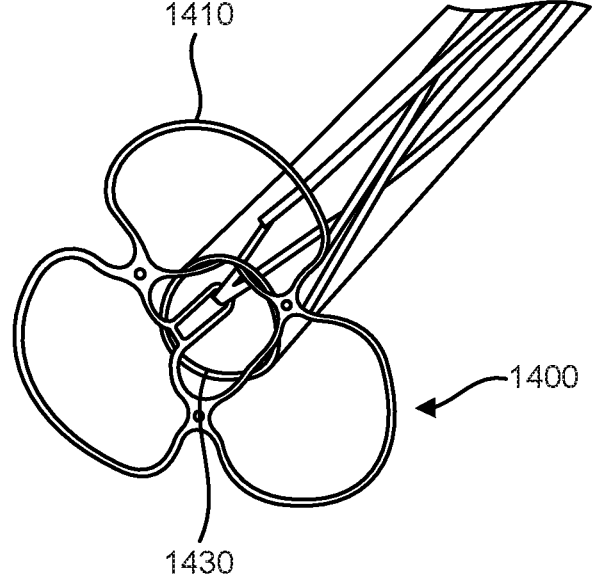
FIG. 14B is an image of the implantable medical device with a first side deployed from the delivery apparatus shown in FIG. 14A, in accordance with an embodiment.

FIG. 14A is an image of an implantable medical device 1400 and a deployment apparatus 1450, in accordance with an embodiment. FIG. 14B is an image of the implantable medical device 1400 with a first side deployed from the deployment apparatus 1450 shown in FIG. 14A, in accordance with an embodiment. As shown, the device 1400 is compressed into a delivery configuration and loaded into the deployment apparatus 1450 to be delivered to a desired treatment location within the patient's body.

In certain instances, the device 1400 is loaded into the deployment apparatus 1450 such that the device 1400 is completely contained within the deployment apparatus 1450, as shown in FIG. 14A.

The device 1400 can be delivered to the desired treatment location while in the delivery configuration. The first frame portion 1410 is then positioned on a first side of the septum and the second frame portion is positioned on a second side of the septum. In some instances, once deployed, the central portion 1430 of the device 1400 can be radially expanded or compressed to adjust the rate of fluid flow through the opening as desired. As described in detail above, the central portion 1430 may include a circumference that approximates a circle in shape. The central portion 1430 may form a polygonal structure, perimeter or boundary that approximates a circle. For example, the central portion 1430 may include 8, 10, 12, 14, 16, 18, 20, 22, 24 or additional sides that form a polygonal perimeter or boundary that approximates a circle in a deployed configuration. The central portion 1430 approximating having a perimeter or boundary that approximates a circle in shape may facilitating collapsing of the device to a delivery configuration while maintain hoop strength and lessen collapsing of the central frame portion 1430 in the deployed configuration.

Figure 15A:
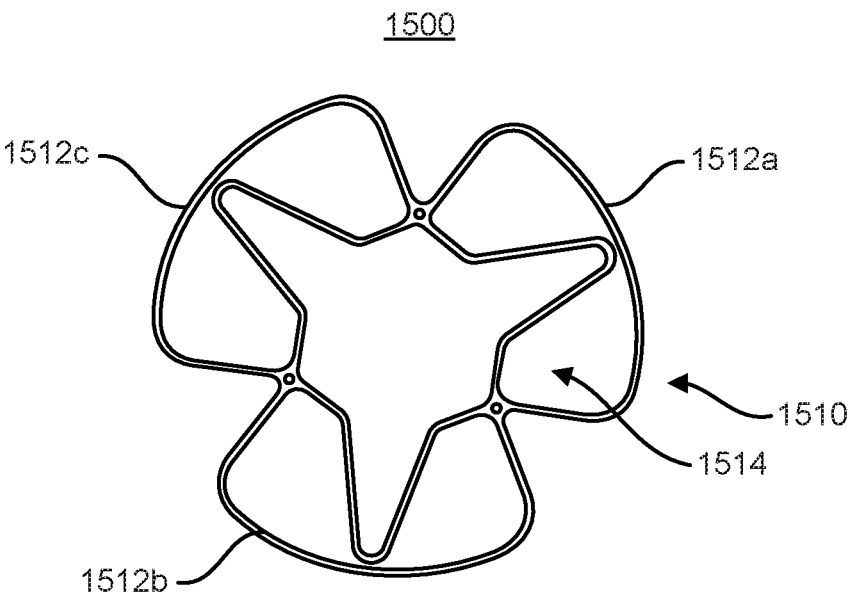
FIG. 15A is an image of the implantable medical device, shown in FIG. 5, in accordance with an embodiment.

FIG. 15A is an image of the implantable medical device 1500 (shown in FIG. 5), in accordance with an embodiment. As shown, the first frame portion 1510 includes three lobes (e.g., a first lobe 1512a, a second lobe 1512b, and a third lobe 1512c) and an inner frame portion 1514. Each of the lobes 1512a, 1512b, and 1512c may be attached to the inner frame portion 1514 such that the lobes are equally spaced around the inner frame portion 1514. In some instances, the inner frame portion 1514 serves as the second frame portion 1520, as shown and discussed with reference to FIG. 15D.

Figure 15B:
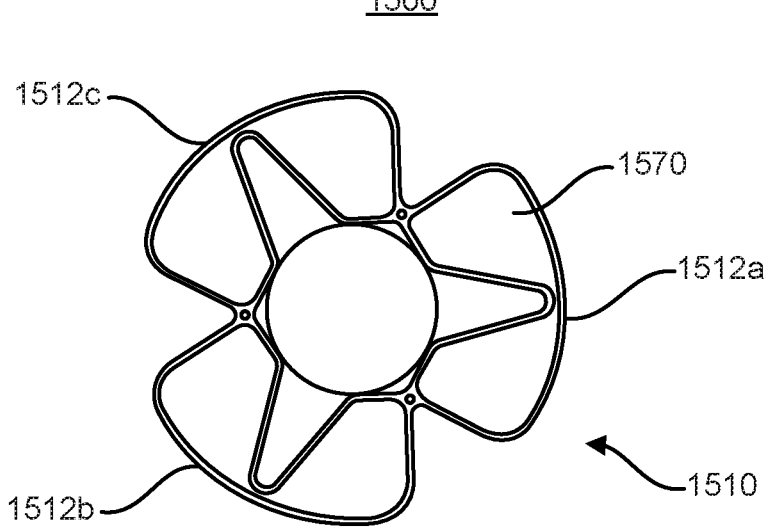
FIG. 15B is an image of the implantable medical, shown in FIG. 15A, including a covering material, in accordance with an embodiment.

FIG. 15B is an image of the implantable medical device 1500 of FIG. 15A including a covering material 1570, in accordance with an embodiment. As shown, the covering material 1570 can be arranged over the first frame portion 1510. In some instances, the covering material 1570 may be attached to one or more of the first lobe 1512a, the second lobe 1512b, and the third lobe 1512c, as shown.

Figure 15C:
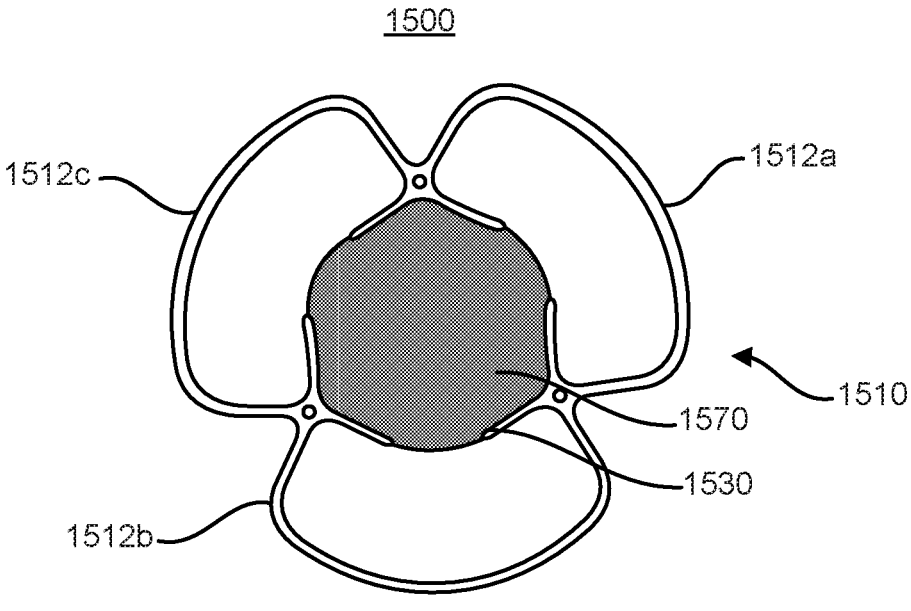
FIG. 15C is an image of a first side of the implantable medical device, shown in FIG. 15A, with a membrane, in accordance with an embodiment.

FIG. 15C is an image of a first side of the implantable medical device 1500, shown in FIG. 15A, including a covering material 1570, in accordance with an embodiment. As shown, in some instances, the covering material 1570 can be arranged over the opening 1530. Thus, the covering material 1530 may act to slow or occlude flow through the device 1500 as desired.

Figure 15D:
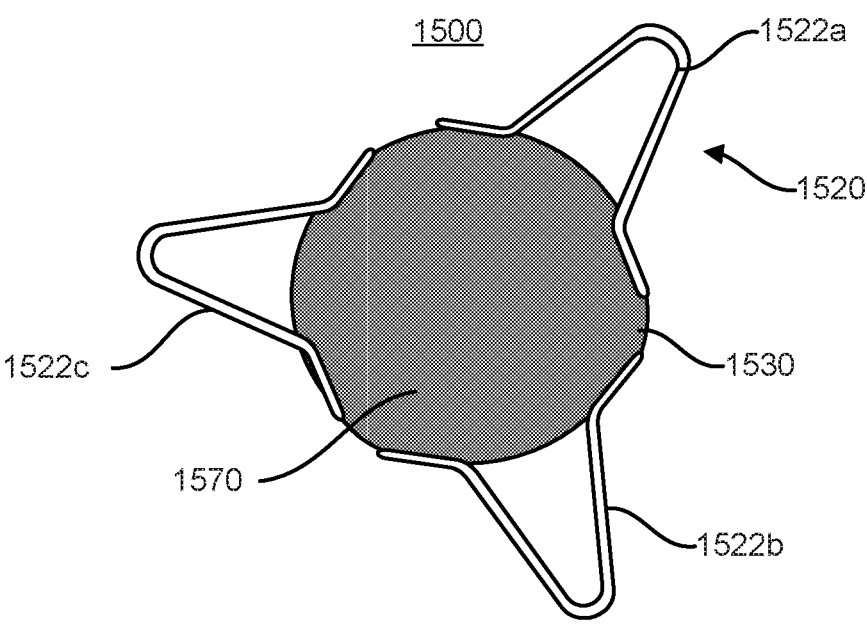
FIG. 15D is an image of a second side of the implantable medical device, shown in FIGS. 15B-C, in accordance with an embodiment.

FIG. 15D is an image of a second side of the implantable medical device 1500, shown in FIG. 15C, in accordance with an embodiment. As shown, the covering material 1570 is arranged over the opening 1530. In various instances, the first, second, and third lobes 1522a, 1522b, 1522c of the second frame portion 1520 may or may not include the covering material 1570. For example, as shown in FIG. 15D, the covering material 1570 is arranged over the opening 1530 but not over the second frame portion 1520, while in other examples, the covering material 1570 may be arranged over both the opening 1530 and the second frame portion 1520.

Figure 16A:
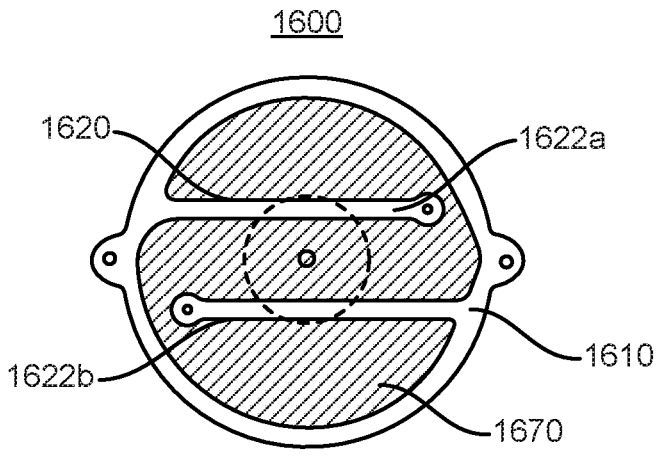
FIG. 16A is an image of an implantable medical device, in accordance with an embodiment.

FIG. 16A is an image of an implantable medical device 1600, in accordance with an embodiment. As shown, the device 1600 includes a first frame portion 1610 and a second frame portion 1620. The second frame portion 1620 includes first and second spokes 1622a and 1622b. In various instances, a covering material 1670 may be arranged over all or a portion of the first frame portion 1610 of the device 1600, as shown.

Figure 16B:
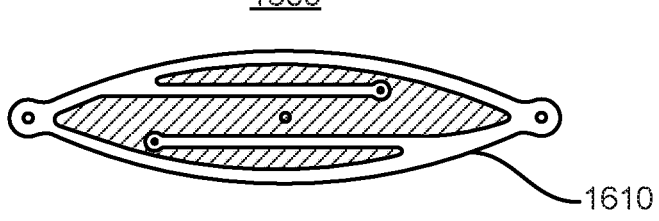
FIG. 16B is an image of a second configuration of the implantable medical shown in FIG. 16A, in accordance with an embodiment.
Figure 16C:
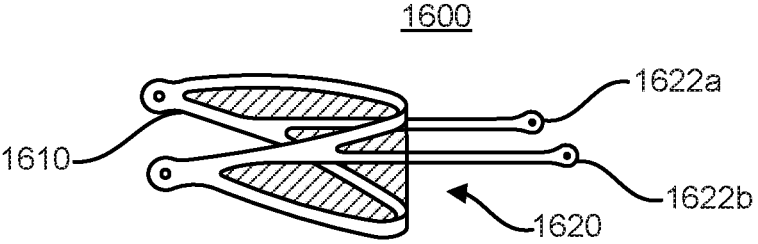
FIG. 16C is an image of the implantable medical device, shown in FIG. 16A, in a deployed configuration in accordance with an embodiment.

FIG. 16B is an image of a second configuration of the implantable medical device 1600 shown in FIG. 16A, in accordance with an embodiment. As shown, the device 1600 is sufficiently flexible such that it is compressible into a delivery configuration. Once positioned at the desired treatment location within the patient's body, the first frame portion 1610 of the device 1600 can be bent upon itself to force the spokes 1622a and 1622b radially outward, as shown in FIG. 16C. The first frame portion 1610 can be positioned on a first side of the septum while the second frame portion 1620 can be arranged on a second side of the septum. When the first frame portion 1610 is released back to its original configuration, the spokes 1622a, 1622b can retain the device 1600 in position in the patient's body.

Figure 17A:
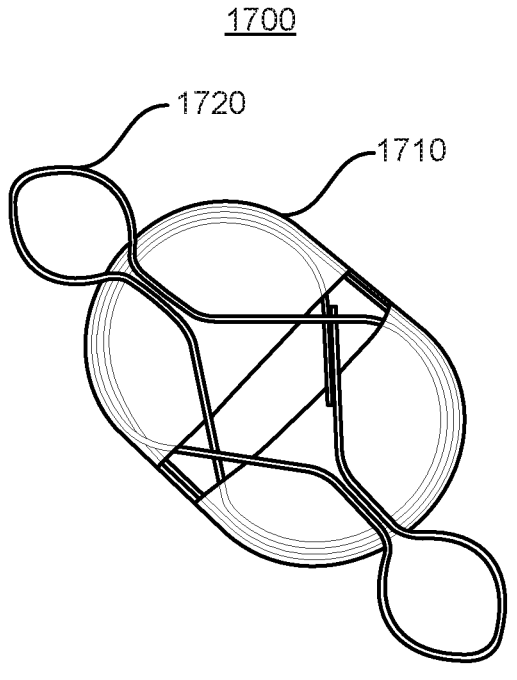
FIG. 17A is an image of an implantable medical device, in accordance with an embodiment.
Figure 17B:
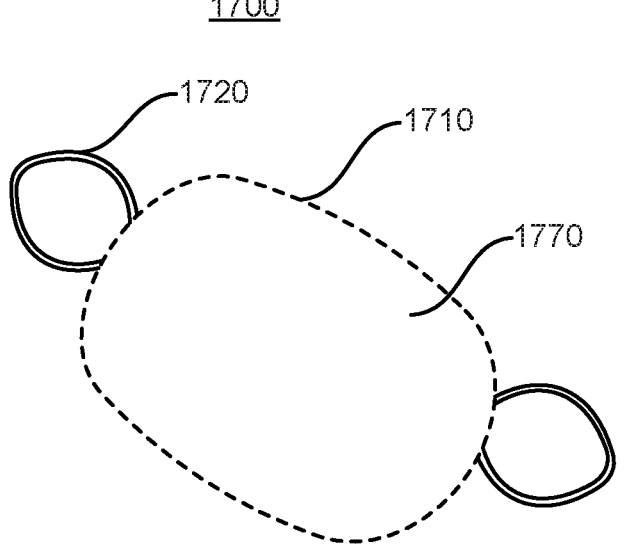
FIG. 17B is an image of the implantable medical device, shown in FIG. 17A, in a deployed configuration, in accordance with an embodiment.

FIG. 17A is an image of an implantable medical device 1700, in accordance with an embodiment. As shown, the first frame portion 1710 of the device 1700 may have no lobes, while the second frame portion 1720 has two or more lobes. For example, the second frame portion 1720 can have a first lobe 1722a and a second lobe 1722b. In some instances, the first frame portion 1710 and/or the second frame portion 1720 can include a covering material 1770. For example, the first frame portion 1710 can include the covering material 1770 as shown in FIG. 17B. However, in other examples, one or more lobes 1722a, 1722b of the second frame portion 1720 may include the covering material 1770, as desired.

Figure 18:
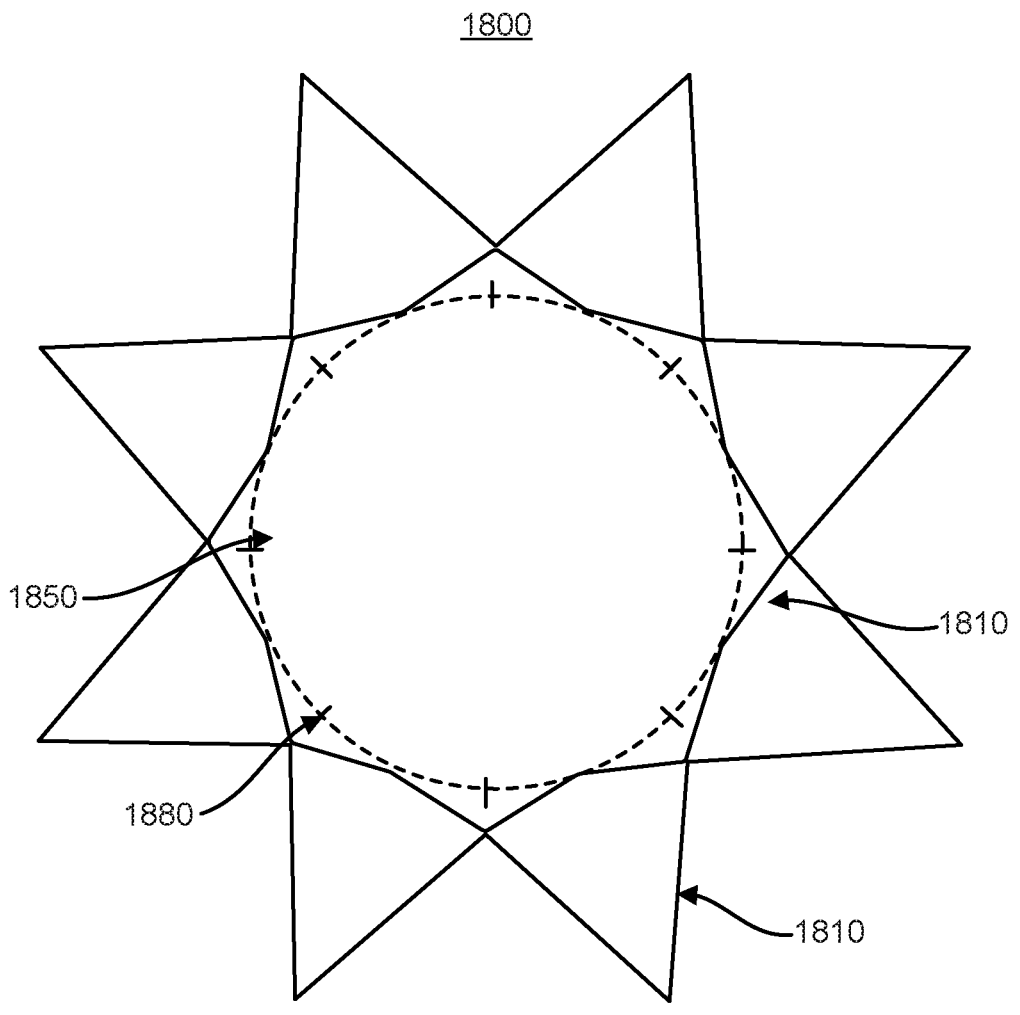
FIG. 18 is an illustration of an implantable medical device, in accordance with an embodiment.

FIG. 18 is an illustration of an implantable medical device 1800, in accordance with an embodiment. The implantable medical device 1800 includes a first frame portion 1810 and a second frame portion 1820 are formed by diverging elements of a continuous or contiguous frame. The first frame portion 1810 and the second frame portion 1820 may be formed of a cut-tube, wound wire, or other similar structure. As discussed in detail above, the first frame portion 1810 and the second frame portion 1820 may include a plurality of lobes and may be interconnected to one another.

In certain instances, the first frame portion 1810 and the second frame portion 1820 are formed by the plurality of diverging elements, which diverge from the first frame portion 1810 and the second frame portion 1820 to form a central frame 1850 that is configured to approximate a circular shape 1880 in a deployed configuration. As shown in FIG. 18, the diverging elements of the frame form a polygonal structure that is the central frame 1850. The number of sides of the polygonal structure that is the central frame 1850 approximate a circular shape 1880 in the deployed configuration.

In certain instances, the central frame 1850 is an opening through the device 1900 for fluid flow. The central frame 1850 forms a boundary or perimeter of that is approximately circular in shape. The first frame portion 1810 and/or the second frame portion 1820, when deployed, may form the central frame 1850 to include a polygonal structure, perimeter or boundary such that the circular shape 1880 is approximated. For example, the central frame 1850 may include 8, 10, 12, 14, 16, 18, 20, 22, 24 or additional sides that form a polygonal structure, perimeter or boundary that approximates the circular shape 1880 in a deployed configuration. The central frame 1850 approximating having a perimeter or boundary that approximates a circle in shape may facilitating collapsing of the device to a delivery configuration while maintain hoop strength and lessen collapsing of the central frame 1850 in the deployed configuration. In the deployed configuration, the first frame portion 1810 may be deployed on one side of a tissue structure and the second frame portion 1820 may be deployed on another side of a tissue structure (e.g., as shown in FIGS. 9B-C.

Figure 19:
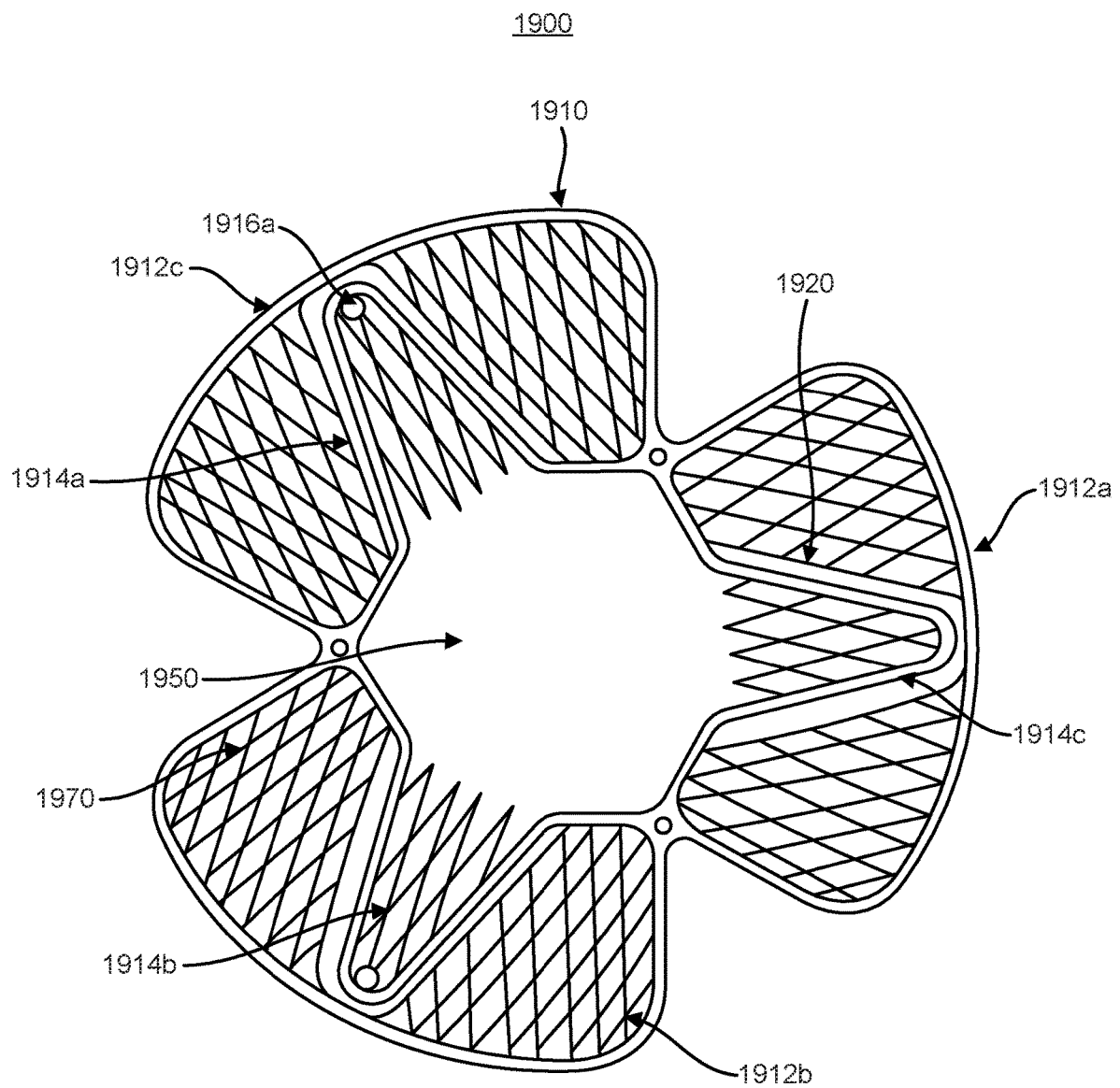
FIG. 19 is an illustration of an implantable medical device, in accordance with an embodiment.

FIG. 19 is an illustration of an implantable medical device 1900, in accordance with an embodiment. As shown, a first frame portion 1910 includes three lobes (e.g., a first lobe 1912a, a second lobe 1912b, and a third lobe 1912c) and an second frame portion 1920. Each of the lobes 1912a, 1912b, and 1912c may be attached to the second frame portion 1920 such that the lobes are equally spaced around the second frame portion 1920, which may also include a set of lobes 1914a, 1914b, and 1914c.

Though not shown in FIG. 19, the first frame portion 1910 and the second frame portion 1920 can have the same or a different number of lobes. For example, in some instances, the first and second frame portions 1910, 1920 each have three lobes. In other instances, the first frame portion 1910 may include two or three lobes while the second frame portion 1920 includes two, four, five or more lobes. In some instances, the first frame portion 1910 can have lobes that are larger, smaller, and/or a different shape than the lobes of the second frame portion 1920. The first frame portion 1910 and the second frame portion 1920 are formed by diverging elements of a continuous or contiguous frame. The first frame portion 1910 and the second frame portion 1920 may be formed of a cut-tube, wound wire, or other similar structure.

In certain instances and as shown, an opening 1950 through the device 1900 includes a circumference that approximates a circle in shape. A boundary or outer circumference of the opening 1950 is approximately circular in shape. The first frame portion 1910 and/or the second frame portion 1920, when deployed, may form a polygonal structure, perimeter or boundary for the opening 1950 that approximates a circle. For example, the opening 1950 may include 8, 10, 12, 14, 16, 18, 20, 22, 24 or additional sides that form a polygonal structure, perimeter or boundary that approximates a circle in a deployed configuration. The opening 1950 approximating having a perimeter or boundary that approximates a circle in shape may facilitate collapsing of the device to a delivery configuration while maintain hoop strength and lessen collapsing of the opening 1950 in the deployed configuration. In the deployed configuration, the first frame portion 1910 may be deployed on one side of a tissue structure and the second frame portion 1920 may be deployed on another side of a tissue structure (e.g., as shown in FIGS. 9B-C.

In certain instances, portions of the first frame portion 1910 and/or the second frame portion 1920 may include a covering material 1970. The covering material 1970 may be configured to inhibit tissue ingrowth (e.g., within the opening 1950 through the device 600). In addition, portions of the covering material 1970 may be arranged on the first frame portion 1910 and/or the second frame portion 1920 between the lobes, as shown. In addition, the covering material 1970 between the lobes may be configured to facilitate tissue ingrowth to enhancing anchoring of the device 600 within the tissue. In the deployed configuration, the first frame portion 1910 may be deployed on one side of a tissue structure and the second frame portion 1920 may be deployed on another side of a tissue structure (e.g., as shown in FIGS. 9B-C.

The devices discussed herein may include a sensor integrated into the respective frame component, for example, for continuous monitoring of various hemodynamic parameters such as pressure, among other parameters, within the patient's body. For example, an antenna or inductor may be wrapped around the perimeter of one of the first and second frame components 110, 120 and the sensor may be attached to the inductor. The sensor may be configured to, for example, sense physiologic properties, such as hemodynamics, biomarkers, sound, pressure, and electrolytes that may be important in diagnosing, monitoring, and/or treating heart disease, heart failure, and/or other cardiovascular disease states.

In certain instances, the devices discussed herein may be capable of delivering a drug to the desired treatment location within the patient's body. For example, the devices may be capable of eluting a drug configured to modulate tissue response. In certain instances, the devices may be coated with a therapeutic coating, drug eluting material or other therapeutic material. In one specific example, the devices can be coated with heparin to facilitate thromboresistance and patency of the devices. Alternatively, or additionally, the devices may include paclitaxel (to modulate tissue/cellular response).

In certain instances, the heparin coating. The heparin coating is utilized to bind heparin molecules to the membrane or covering material. For further reference regarding a heparin coated membrane or covering material, reference may be made to U.S. Pat. No. 6,461,665 ("Scholander") for the specific teachings of antithrombogenic activity of surface immobilized heparin, which is incorporated herein by reference. In certain instances, the heparin coating may be CARMEDA® BioActive Surface (CBAS® Heparin Surface).

In certain instances, the heparin coating may be applied to the membrane or covering material in one or more layers. The chemical constituents of the covering material in each layer can be the same or different. In some instances, the covering material is cross-linked to itself or other covering materials in other layers. The cross-linking bonds can be covalent or ionic. The heparin covering may form at least one layer on at least a portion of the membrane or covering material and may cross-link to itself or other layers of the covering. The cross-linking can be covalent, ionic, or both. For reference regarding the application of layers of heparin to the membrane or covering material reference may be made to U.S. Pat. No. 9,399,085 (Cleek et al.), which is incorporated herein by reference.

Suitable membrane materials for the membrane or covering material include, but are not limited to, polymers such as olefin, PEEK, polyamide, polyurethane, polyester, such as polyethylene terephthalate (PET), polyethylene, polypropylene, polyurethane, silicone, fluorinated ethylene propylene (FEP), polytetrafluoroethylene (PTFE), expanded polytetrafluoroethylene (ePTFE), and fluoroelastomers, such as tetrafluoroethylene/polymethylvinylether (TFE/PMVE) copolymers. In certain instances, the membrane or covering material may include is the elastomeric material (e.g., TFE/PMVE).

In some embodiments, bioresorbable or bioabsorbable materials may be used, for example a bioresorbable or bioabsorbable polymer. In some embodiments, the membrane can comprise a fluoropolymer, such as described in one or more of U.S. Pat. Nos. 7,049,380; 7,462,675; and 8,048,440, the contents of which are each incorporated by reference herein. In some embodiments, the membrane can comprise Dacron, polyolefins, carboxy methylcellulose fabrics, polyurethanes, or other woven or film elastomers. In some embodiments, the membrane or covering material can include knits or fibers. The membrane or covering material may be woven or non-woven in various embodiments including wires for example. In some embodiments, the membrane or covering material may be formed of a combination and/or copolymer of fluoropolymers or blends thereof.

Examples of synthetic polymers (which may be used as a membrane component) include, but are not limited to, nylon, polyacrylamide, polycarbonate, polyformaldehyde, polymethylmethacrylate, polytetrafluoroethylene, polytrifluoro-chlorethylene, polyvinylchloride, polyurethane, elastomeric organosilicon polymers, polyethylene, polypropylene, polyurethane, polyglycolic acid, polyesters, polyamides, their mixtures, blends and copolymers are suitable as a membrane material.

In some embodiments, the membrane is configured to inhibit, filter, modulate, or substantially modulate the passage of fluids and/or materials (such as blood and/or thrombus) through the membrane. In some embodiments, the membrane is configured to induce rapid tissue ingrowth therein. In an embodiment, the membrane provides for a blood or body fluid impermeable membrane that occludes the flow of blood or bodily fluids through the membrane yet promotes the ingrowth and endothelialization. The membrane can have a microporous structure that provides a tissue ingrowth scaffold for durable occlusion and supplemental anchoring strength of frames. In some embodiments, the membrane may be a porous member. Pores of the membrane may be sized to substantially, or in some examples completely, help prevent passage of blood, other bodily fluids, and emboli. In some implementations, the membrane prevents or substantially prevents passage of blood, other bodily fluids, thrombi, emboli, or other bodily materials through the membrane.

Nitinol (NiTi) may be used as the material of the frames discussed herein. In other instances, the frames may be formed from other materials such as stainless steel, L605 steel, polymers, MP35N steel, polymeric materials, Pyhnox, Elgiloy, or any other appropriate biocompatible material, and combinations thereof, can be used as the material of the frames. The super-elastic properties and softness of NiTi may enhance the conformability of the frames. In addition, NiTi can be shape-set into a desired shape. That is, NiTi can be shape-set so that the frame tends to self-expand into a desired shape when the frames is unconstrained, such as when the frame is deployed out from a delivery system. More specifically, the frame (made of NiTi) may have a spring nature that allows the frame to be elastically collapsed or "crushed" to a low-profile delivery configuration for loading in a delivery system, and then to reconfigure to the expanded configuration upon emergence from the delivery system. The frames, discussed herein, may be generally conformable, fatigue resistant, and elastic such that the frames may conform to the topography of the surrounding tissue when the occlusive device is deployed in a patient. In certain embodiments, bioresorbable or bioabsorbable materials may be used for the frame or a portion thereof, including for example, a bioresorbable or bioabsorbable polymer.

The membrane components, as discussed herein, may be attached to the self-expanding frame components by using a coupling member that is generally a flat ribbon or tape having at least one generally flat surface. In certain instances, the tape member is made from expanded PTFE (ePTFE) coated with an adhesive. The adhesive may be a thermoplastic adhesive. In certain instances, the thermoplastic adhesive may be fluorinated ethylene propylene (FEP). More specifically, an FEP-coated side of the ePTFE may face toward and contacts an exterior surface of the self-expanding frame components and membrane component, thus attaching the self-expanding frame components to the membrane component. Materials and method of attaching frame components to the membrane is discussed in U.S. Pat. No. 6,042,605 to Martin, incorporated by reference herein for all purposes.

In addition, nitinol (NiTi) may be used as the material of the frame or stent (and any of the frames discussed herein), but other materials such as, but not limited to, stainless steel, L605 steel, polymers, MP35N steel, polymeric materials, Pyhnox, Elgiloy, or any other appropriate biocompatible material, and combinations thereof, can be used as the material of the frame. The super-elastic properties and softness of NiTi may enhance the conformability of the stent. In addition, NiTi can be shape-set into a desired shape. That is, NiTi can be shape-set so that the frame tends to self-expand into a desired shape when the frame is unconstrained, such as when the frame is deployed out from a delivery system.

A variety of materials variously metallic, super elastic alloys, such as Nitinol, are suitable for use in these frame components. Primary requirements of the materials are that they be suitably springy even when fashioned into very thin sheets or small diameter wires. Various stainless steels which have been physically, chemically, and otherwise treated to produce high springiness are suitable as are other metal alloys such as cobalt chrome alloys (e.g., ELGILOY®), platinum/tungsten alloys, and especially the nickel-titanium alloys (e.g., Nitinol).

The invention of this application has been described above both generically and with regard to specific embodiments. It will be apparent to those skilled in the art that various modifications and variations can be made in the embodiments without departing from the scope of the disclosure. Thus, it is intended that the embodiments cover the modifications and variations of this invention provided they come within the scope of the appended claims and their equivalents.

What is claimed is:

1. An implantable medical device, comprising:
a first frame portion having at least three lobes;
a second frame portion arranged within the first frame portion, wherein the first frame portion and the second frame portion are coplanar with one another within a plane when the device is in an unconstrained configuration, wherein the plane is orthogonal to a longitudinal axis of the implantable medical device, and wherein at least a portion of the first and second frame portions are nonplanar with one another when the device is in a delivery configuration; and
a plurality of diverging elements arranged between the first frame portion and the second frame portion, the plurality of diverging elements diverge from the first frame portion and the second frame portion to form a central frame with at least six diverging points in a deployed configuration.

2. The device of claim 1, wherein the first frame portion and the second frame are contiguous with one another.

3. The device of claim 1, wherein the central frame defines an opening that is hexagonal in shape when the device is in a deployed configuration.

4. The device of claim 1, wherein the first frame portion is located on a first side of a septum, the second frame portion is located on a second side of the septum, and the plurality of diverging elements form a fluid flow path therethrough.

5. The device of claim 4, wherein the first and second frame portions are sufficiently flexible to conform to an anatomy of the septum.

6. The device of claim 1, wherein the second frame portion includes at least three lobes.

7. The device of claim 1, wherein the first frame portion has a first geometry and the second frame portion has a second geometry that is different from the first geometry.

8. The device of claim 1, wherein the first frame portion includes six lobes.

9. The device of claim 1, wherein each of the lobes of the second frame portion comprises an eyelet configured to aid in delivery of the device.

10. The device of claim 1, further comprising a covering material arranged on at least a portion of the device.

11. The device of claim 10, wherein the first frame portion includes the covering material and the second frame portion is free of the covering material.

12. The device of claim 11, wherein the covering material includes expanded polytetrafluoroethylene (ePTFE).

13. The device of claim 1, wherein the first frame portion and the second frame portion are unitary such that the device is formed of a single wire.

14. The device of claim 1, further comprising at least one of a coating of heparin to facilitate thromboresistance and patency of the device and a coating of paclitaxel to modulate tissue/cellular response.

15. The device of claim 1, wherein the longitudinal axis extends through a center of a lumen defined by the implantable medical device and the plane extends through a portion of the lumen.

16. The device of claim 1, wherein the at least three lobes extend perpendicularly to the longitudinal axis in the unconstrained configuration.

* * * * *